United States Patent
Crouch et al.

(10) Patent No.: US 6,911,319 B2
(45) Date of Patent: *Jun. 28, 2005

(54) METHODS AND KITS FOR DETECTING PROTEIN KINASES

(75) Inventors: Sharon Patricia Mary Crouch, Nottingham (GB); Kevin John Slater, Nottingham (GB)

(73) Assignee: Lumitech (UK) Limited, Nottingham (GB)

(*) Notice: Subject to any disclaimer, the term of this patent is extended or adjusted under 35 U.S.C. 154(b) by 125 days.

This patent is subject to a terminal disclaimer.

(21) Appl. No.: 10/426,973

(22) Filed: May 1, 2003

(65) Prior Publication Data

US 2004/0077030 A1 Apr. 22, 2004

Related U.S. Application Data

(63) Continuation of application No. 10/014,816, filed on Dec. 14, 2001, now Pat. No. 6,599,711.

(30) Foreign Application Priority Data

Dec. 15, 2000 (GB) .............................. 0030727

(51) Int. Cl.[7] .......................... C12Q 1/48; C12Q 1/00; C12Q 1/66; C12Q 1/37
(52) U.S. Cl. .............................. 435/15; 435/21; 435/4; 435/8; 435/23
(58) Field of Search ................ 435/15, 21, 4

(56) References Cited

U.S. PATENT DOCUMENTS

| | | | |
|---|---|---|---|
| 4,235,961 A | 11/1980 | Lundin | 435/8 |
| 4,246,340 A | 1/1981 | Lundin et al. | 435/8 |

(Continued)

FOREIGN PATENT DOCUMENTS

| | | |
|---|---|---|
| DE | 29 08 054 | 9/1980 |
| DE | 694 12 790 T2 | 1/1993 |
| EP | 0 022 432 A | 1/1981 |

(Continued)

OTHER PUBLICATIONS

Sqirrell et al., Journal Defense Sciense, 2:229–297 (1997).
T. Halonen, et al., "Bioluminescent Assay of Total and Brain–Specific Creatine Kinase Activity in Cerebrospinal Fluid," Journal of Neurochemistry, vol. 39, pp. 36–43 (Nov. 1, 1982).
Tecan, "A New Generic Luminescent Protein Kinase Assay Suitable for High Throughout Screening," Ultra Evolution, application note released in cooperation with Cambrex, www.tecan.com.
R. Somberg, Ph.D., et al., "A Universal Kinase Assay for a World of Kinases," Promega, ppg. 14–17, No. 83 2003, www.promega.com.

(Continued)

Primary Examiner—Louise N. Leary
(74) Attorney, Agent, or Firm—Banner & Witcoff, Ltd.

(57) ABSTRACT

A method for measuring protein kinase activity comprising:
(a) providing a first solution comprising ATP and a protein kinase to be tested, and a second solution comprising ATP in the absence of said kinase to be tested;
(b) adding a substrate capable of being phosphorylated by the protein kinase to be tested to the first and second solutions of step (a);
(c) measuring the concentration of ATP and/or ADP, or the rate of change thereof with respect to time, in each of the reaction mixtures formed in step (b) using a bioluminescence reaction; and
(d) using the information about the concentration of ATP and/or ADP to determine the activity of the protein kinase to be tested.

29 Claims, 24 Drawing Sheets

U.S. PATENT DOCUMENTS

| | | | |
|---|---|---|---|
| 4,286,057 A | 8/1981 | Wulff et al. | 435/8 |
| 5,330,906 A | 7/1994 | Kajiyama et al. | 435/189 |
| 5,374,534 A | 12/1994 | Zomer et al. | 435/8 |
| 5,583,024 A | 12/1996 | McElroy et al. | 435/189 |
| 5,648,232 A | 7/1997 | Squirrell | 435/34 |
| 5,759,795 A | 6/1998 | Jubin | 435/210 |
| 5,925,558 A | 7/1999 | Tsien et al. | 435/252.3 |
| 6,074,859 A | 6/2000 | Hirokawa et al. | 435/189 |
| 6,310,060 B1 | 10/2001 | Barrett et al. | 514/231.2 |
| 6,503,723 B1 | 1/2003 | Van Lune et al. | |
| 6,599,711 B2 * | 7/2003 | Crouch et al. | 435/15 |
| 2002/0172991 A1 | 11/2002 | Crouch et al. | 435/15 |

FOREIGN PATENT DOCUMENTS

| | | |
|---|---|---|
| EP | 0 301 541 | 2/1989 |
| EP | 0 449 621 B1 | 8/1996 |
| EP | 0 794 260 A | 9/1997 |
| GB | 2055200 A | 2/1981 |
| GB | 2323167 B | 6/1999 |
| WO | WO 94/17202 | 8/1994 |
| WO | WO 95/18853 | 7/1995 |
| WO | WO 96/22376 | 7/1996 |
| WO | WO-98/09169 A1 | 3/1998 |
| WO | WO 98/28437 | 7/1998 |
| WO | WO 98/46729 | 10/1998 |
| WO | WO 99/02697 | 1/1999 |
| WO | WO 99/37799 | 7/1999 |
| WO | WO 99/41408 | 8/1999 |
| WO | WO 00/70082 | 11/2000 |

OTHER PUBLICATIONS

Molecular Probes, "ATP Determination Kit (A–6608)," ATP Determination Kit (revised: Jul. 22, 1999), with English translation of D5.

E.M. Golding et al., Adjustment of K'to varying pH and pMg for the creatine kinase, adenylate kinase and ATP hydrolysis equilibria permitting quantitative bioenergetic assessment, 1995, pp. 1775–1782, vol. 198, The Journal of Experimental Biology.

W.E. Teague, Jr. et al., Adjustment of K'for the creatine kinase, adenylate kinase and ATP hydrolysis equilibria to varying temperature and ionic strength, 1996, pp. 509–512, vol. 199, The Journal of Experimental Biology.

T. Decker et al., A quick and simple method for the quantitation of lactate dehydrogenase release in measurements of cellular cytotoxicity and tumor necrosis factor (TNF) activity, 1988, pp. 61–69, vol. 15, Journal of Immunological Methods.

M.M. Nociari et al, A novel one–step, highly sensitive fluorometric assay to evaluate cell–mediated cytotoxicity, 1998, pp. 157–167, vol. 213, Journal of Immunological Methods.

M. Bachy et al., Beta galactosidase release as an alternative to chromium release in cytotoxic T–cell assays, 1999, pp. 37–46, vol. 230, Journal of Immunological Methods.

N. Kasatori et al., Cytotoxicity test based on luminescent assay of alkaline phosphatase released from target cells, 1994, pp. 1050–1054, vol. 42, Rinsho Buori.

S. D'Atri et al., A miniaturized cell–mediated cytotoxicity assay with human effector mononuclear cells, 1986, pp. 383–390, vol. 5, Int. J. Tiss. Reac. VIII.

G. Feutren et al., Immune lysis of hepatocytes in culture: accurate detection by aspartate aminotransferase release measurement, 1984, pp. 85–94, vol. 75, Journal of Immunological Methods.

J.G. Pastorino et al., Functional consequences of the sustained or transient activation by bex of the mitochondrial permeability transition pore*, Oct. 29, 1999, pp. 31734–31739, vol. 274, No. 44, The Journal of Biological Chemistry.

G. Sala–Newby et al., Engineering firefly luciferase as an indicator of cyclic AMP–dependent protein kinase in living cells, Jul. 1992, pp. 241–244, vol. 307, No. 2, FEBS 11346.

B.R. Branchini et al., The role of lysine 529, a conserved residue of the acyl–adenylate–forming enzyme superfamily, in firefly luciferase, 2000, pp. 5433–5440, vol. 39, No. 18, Biochemistry 2000.

B.R. Branchini et al., Site–directed mutagenesis of firefly luciferase active site amino acids: a proposed model for bioluminescence color, 1999, pp. 13223–13230, vol. 38, No. 40, Biochemistry.

P.J. White et al., Improved thermostability of the North American firefly luciferase: saturation mutagenesis at position 354, 1996, pp. 343–350, vol. 319, Biochem. J.

J.H. Devine et al., Luciferase from the East European firefly luciola mingrelica: cloning and nucleotide sequence of the cDNA, overexpression in *Escherichia coli* and purification of the enzyme, 1993, pp. 121–132, vol. 1173, Biochimica et Biophysica Acta.

C.B. Cohen et al., A microchip–based enzyme assay from protein kinase A, 1999, pp. 89–97, vol. 273, Analytical Biochemistry.

J. Eu et al., Homogeneous bioluminescence assay for galactosuria: interference and kinetic analysis, 1999, pp. 168–176, vol. 271, Analytical Biochemistry.

C. Lehel et al., A chemiluminescent microtiter plate assay for sensitive detection of protein kinase activity, 1997, pp. 340–346, vol. 244, Analytical Biochemistry.

H. Tatsumi et al., Construction of biotinylated firefly luciferases using biotin acceptor peptides, 1996, pp. 176–180, vol. 243, Analytical Biochemistry.

A. Thore, Technical aspects of the bioluminescent firefly luciferase assay of ATP, 1979, pp. 30–34, vol. 26, No. 2, Science Tools.

T. Olsson et al., Leakage of adenylate kinase from stored blood cells, 1983, pp. 437–445, vol. 5, Journal of Applied Biochemistry.

M. Karp et; al., A streptavidin–luciferase fusion protein: comparisons and applications, 1999, pp. 101–104, vol. 16, Biomolecular Engineering.

L. Chinsoo Cho, To lap or not to lap, 1996, pp. 120–124, vol. 1, The Oncologist.

Karamohamed et al., "Real–time Bioluminometric Method for Detection of Nucleoside Diphosphate Kinase Activity", *Biotechniques*, 26:728–734 (1999).

Handa et al., "Assay of Adenosine 3', 5' Cyclic Monophosphate by Stimulation of Protein Kinase: A Method Not Involving Radioactivity", *Analytical Biochemistry*, 102:332–339 (1980).

* cited by examiner

METHODS AND KITS FOR DETECTING PROTEIN KINASES

This application is a continuation of Ser. No. 10/014,816 filed on Dec. 14, 2001, now U.S. Pat. No. 6,599,711, which application claimed the benefit of GB 0030727.2 filed in Great Britain on Dec. 15, 2000.

BACKGROUND OF THE INVENTION

1. Field of the Invention

The present invention relates to methods for detecting protein kinase activity and kits for performing such methods.

2. Description of Related Art

Protein kinases play crucial roles in the modulation of a wide variety of cellular events. These enzymes act by transferring phosphate residues to certain amino acids in intracellular polypeptides, to bring about the activation of these protein substrates, and set in motion a cascade of activation controlling events including the growth, differentiation and division of cells. Protein kinases have been extensively studied in the field of tumour biology. A lack of controlled activity of kinases in cells is believed to lead to the formation of tumours. The pharmaceutical industry is constantly in search of drugs that target these kinases, to help with the treatment of a wide variety of tumours. There are at least 1200 protein kinases that are involved in the regulation of cell functions. They occur as both transmembrane and cytosolic enzymes and they phosphorylate serine, threonine and tyrosine amino acid residues. Based on these substrate specificities the kinases are divided into two groups, the serine/threonine kinases and tyrosine kinases. This has led to the development of a number of techniques that focus on the ability of these proteins to take a phosphate group and attach it to a protein/peptide.

One of the most widely used techniques is a radio-isotope method, that utilises either $^{32}P$ or $^{33}P$ gamma phosphates. In the presence of an active kinase, the labelled phosphate is transferred from the ATP to the protein or peptide substrate. These assays need to be performed in the presence of ATP labelled to a high specific activity. This results from keeping the concentration of unlabelled ATP in the micromolar concentration range. Also in order to achieve the required sensitivity the peptide substrate has to be used at high concentrations (5–20 $\mu$M). The increased radioactivity on the resulting phosphoproteins can then be detected using scintillation counters after capture on phosphocellulose paper.

Other methods include immunoprecipitation procedures. During these assays the kinase, ATP and substrate reaction is allowed to proceed and is then stopped using a buffer, such as Laemmli buffer. The protein is then run out using SDS/PAGE electrophoresis. The gel is then blotted onto a nitrocellulose membrane and probed for phosphorylated substrate, using an antibody to the phosphorylated amino acid of choice. The presence of the phosphorylated band can be visualised using a secondary antibody conjugated to horseradish peroxidase, followed by the use of a chemiluminescence detection system, and exposure onto photographic film. As in the case of many of the methods that have been proposed as an alternative to the radioisotope assays, however, the above western blotting technique lacks sensitivity and is quite laborious.

The use of luminescent detection, either by bioluminescence or chemiluminescence allows for a highly sensitive detection system. Lehel et al. (1997) *Anal. Biochem.* 244, 340–346 reported the use of a chemiluminescent microtitre plate assay for detection of protein kinase activity. This assay is based on the use of biotinylated substrate peptides captured on a streptavidin-coated microplate, together with monoclonal antibodies. The authors chose protein kinase A (PKA) to develop the assay, but also found reliable results with chose protein kinase C (PKC), calcium/calmodulin-dependent protein kinase II, receptor interacting protein and src activities. These assays were performed in the presence of 20 $\mu$M ATP and the kinase of interest +/− inhibitor, the kinase reaction was allowed to proceed to completion. The plates were then washed prior to antibody binding and chemiluminescence detection with a secondary antibody conjugated to horseradish peroxidase with chemiluminescence determined using a Tropix (RTM) (USA) chemiluminescent substrate kit. This assay still relies upon the availability of specific substrates, and also antibodies to the phosphoproteins generated.

Another approach that has been taken, is to adopt microchip-based technology. Cohen et al. (1999) *Anal. Biochem.* 273, 89–97, reported an assay for PKA based on photolithographic techniques. Performing an on-chip electrophoretic separation of the fluorescently labelled peptide substrate and product allowed for determination of the movement of the phosphate group from ATP to the serine residue of the heptapeptide, Kemptide. This technology was developed for the detection of PKA activity.

Eu et al (1999) *Anal. Biochem.* 271, 168–176 describe a method in which the measurement of ATP via bioluminescence is related to the amount of substrate (galactose) which is present in a urine sample.

Sala-Newby & Campbell (1992) *FEBS Lett* 307, 241–244 describe the use of a firefly luciferase which was engineered to contain a protein kinase A recognition site RRFS and to lack the C-terminal peroxisomal signal of native luciferase. The mutant luciferase was expressed in COS cells and used to detect and quantify protein kinase A activation by cyclic AMP in those cells.

It will be appreciated that the above method is extremely specific, being useful only for protein kinase A activation by cyclic AMP. Hence, it suffers from the same problems as the protein kinase detection systems described above which are based on the specific enzymes and substrates with which they react.

There are no assays that have the ability to determine kinase activity irrespective of the kinase family or the amino acid residues that are phosphorylated. This is due to the fact that all the methods currently available focus on the specific enzymes and substrates involved.

The present invention seeks to provide methods for measuring protein kinase activity which are not specific for a single protein kinase, but rather can be used as a general means of measuring the activity of a wide range of protein kinases.

DETAILED DESCRIPTION OF THE INVENTION

Figure 1:
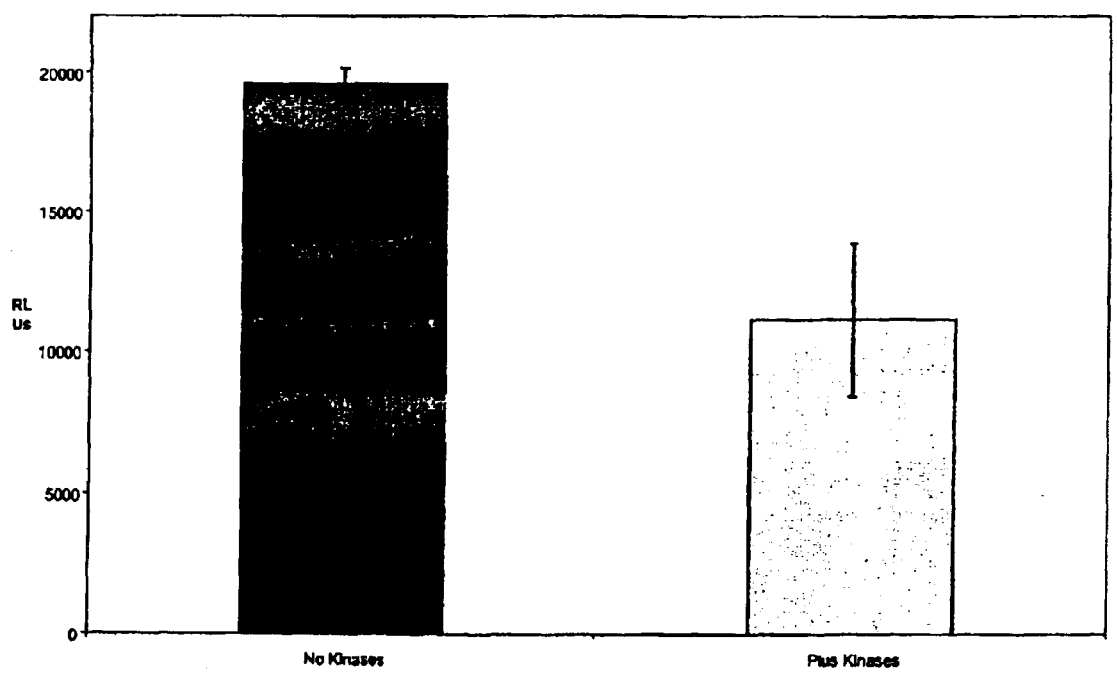
FIG. 1: Shows the drop in ATP light output (relative light units; RLUs) associated with the protein kinase JNK-1. The means of three separate experiments±standard error of the mean (SEM) are shown. These are the results from the data generated in the presence of 200 mM Hepes.

According to the invention there is provided a method for measuring protein kinase activity, said method comprising:
(a) providing a first solution comprising ATP and a protein kinase to be tested, and a second solution comprising ATP in the absence of said protein kinase to be tested;
(b) adding a substrate capable of being phosphorylated by the protein kinase to be tested to the first and second solutions of step (a);
(c) measuring the concentration of ATP and/or ADP, or the rate of change thereof with respect to time, in each of the reaction mixtures formed in step (b) using a bioluminescence reaction; and
(d) using the information about the concentration of ATP and/or ADP to determine the activity of the protein kinase to be tested.

The kinase is preferably activated prior to step (a) by phosphorylation. Kinases are involved in very complex intracellular signalling cascades. On binding of an agonist to a cell membrane receptor a number of phosphorylation events are very rapidly set in motion. In quiescent cells, a number of kinases are in their inactive form and require phosphorylation in order to allow these enzymes to then phosphorylate their substrates. By a domino-like effect, activation of one component of the pathway may provide a large amplification of the signal. For example, Raf is a serine/threonine kinase that phosphorylates and activates MEK (MAPK kinase). MEK, in turn, is a dual tyrosine/threonine kinase which will activate MAPK (Erk-1 and Erk-2) by phosphorylation of the tyrosine and threonine residues. The MAPKs, in turn, are then activated such that they can phosphorylate their substrates, i.e. myelin basic protein.

Commercially available kinases can be obtained in their active form (already phosphorylated by the suppliers) or in their inactive form. The latter require phosphorylation by another kinase which would be upstream from them in the signal transduction pathway.

Since the methods of the invention are not selective for particular types of kinases (i.e. serine/threonine vs. tyrosine), they can be used to monitor the step-wise activation of all the kinases in a particular pathway, for example by measuring the reduction in ATP seen when MEK phosphorylates Erk-1, which in turn phosphorylates myelin basic protein.

A second aspect the invention provides a method for identifying a compound which modulates the activity of a protein kinase, said method comprising:

(a) providing a first solution comprising ATP, a protein kinase and a compound to be tested, and a second solution comprising ATP and the protein kinase in the absence of said compound to be tested;

(b) adding a substrate capable of being phosphorylated by said protein kinase to the first and second solutions of step (a);

(c) measuring the concentration of ATP and/or ADP, or the rate of change thereof with respect to time, in each of the reaction mixtures formed in step (b) using a bioluminescence reaction;

(d) using the information about the concentration of ATP and/or ADP to determine the activity of the protein kinase in the first and second solutions;

(e) comparing the activity of the protein kinase in the first solution with the activity of the protein kinase in the second solution to identify compounds which modulate the activity of a protein kinase, whereby the compound to be tested is identified as a protein kinase modulator if the activity of the protein kinase in the first solution is different from the activity of the protein kinase in the second solution.

Exemplary kinase/substrate combinations for use in the methods of the invention include JNK-1/c-jun, JNK-2/c-jun, MAP Kinase-1 (ERK-1)/myelin basic protein, MAP Kinase-2 (ERK-2)/myelin basic protein, PKA/Kemptide, MEK-1/inactive MAP Kinase-2 (ERK-2), JNK2α2/ATF-2, JNK2α2/c-jun, SAPK-3/myelin basic protein, SAPK-4/ myelin basic protein and raf-1/ inactive MEK-1.

By "modulate" we include the meaning that the activity of the protein kinase is increased or decreased or prevented/ inhibited in the presence of the test compound. Thus, the methods of the invention may be used to determine whether a compound is an inhibitor or activator of a protein kinase.

The compound to be tested is identified as a protein kinase inhibitor if the activity of the kinase in the first solution is lower than the activity of the kinase in the second solution. Preferably, the compound to be tested is identified as a protein kinase inhibitor if the activity of the kinase in the first solution is less than 90% of the activity of the kinase in the second solution. More preferably, the compound to be tested is identified as a protein kinase inhibitor if the activity of the kinase in the first solution is less than 80%, 70%, 60%, 50%, 40%, 30%, 20% or 10% of the activity of the kinase in the second solution. Most preferably, the compound to be tested is identified as a protein kinase inhibitor if the activity of the kinase in the first solution is less than 50% of the activity of the kinase in the second solution.

Likewise, the compound to be tested is identified as a protein kinase activator if the activity of the kinase in the first solution is higher than the activity of the kinase in the second solution. Preferably, the compound to be tested is identified as a protein kinase activator if the activity of the kinase in the first solution is more than 10% greater that the activity of the kinase in the second solution. More preferably, the compound to be tested is identified as a protein kinase inhibitor if the activity of the kinase in the first solution is more than 20%, 30%, 40%, 50%, 75%, 100% or 200% greater than the activity of the kinase in the second solution. Most preferably, the compound to be tested is identified as a protein kinase activator if the kinase in the first solution at least 50% greater than the activity of the kinase in the second solution.

Conveniently, the first and second solutions of step (a) of the methods of the invention are substantially cell-free.

Steps (a) to (d) of the method according to the second aspect of the invention may be repeated one or more times using a different kinase and its corresponding substrate each time.

Compounds which increase the activity of a protein kinase may find utility in medicine, especially the study of cancers and may be useful as therapeutic agents. Compounds which decrease or prevent/inhibit the activity of a protein kinase may also find utility in such applications.

Preferably, the first and second solutions of step (a) comprise a buffer, conveniently Hepes buffer.

Advantageously, steps (a) to (c) are carried out consecutively.

It will be appreciated by persons skilled in the art that, following addition of the substrate in step (b), the reaction may be allowed to proceed for various durations and at different temperatures prior to step (c). Advantageously, following addition of the substrate in step (b), the reaction mixture is allowed to react for 10 minutes at 30° C. prior to step (c). Conveniently, following addition of the substrate in step (b), the reaction mixture is allowed to react for 10 minutes at 30° C. or for 1 hour at room temperature prior to step (c).

Preferably, step (c) of the methods of the invention comprises:

(i) adding a bioluminescent reagent comprising luciferin or a derivative thereof and a luciferase to said reaction mixtures, said luciferin or a derivative thereof emitting light in a bioluminescent reaction with the luciferase in the presence of ATP; and (ii) measuring the intensity of light emitted by the resultant bioluminescent reaction, or its change with respect to time, as a measure of ATP concentration.

The bioluminescent reagent of step (c) can be any of the luciferin/luciferase general type. The active substrate is D-luciferin or a derivative thereof. U.S. Pat. No. 5,374,534 discloses D-luciferin derivatives which may be used with luciferase in the methods of the invention. Any other derivative can be used.

The luciferase enzyme is preferably obtained naturally, especially from fireflies and most especially *Photinus pyralis*. However, the source of the luciferase is not critical, so long as it reacts with luciferin (or a derivative thereof) and ATP in the bioluminescent reaction. Examples are luciferases from *Luciola cruciata, Diptera spp.* and *Coleoptera spp.*

Synthetic, for example, recombinant luciferase can be used in the invention. It is described by Devine et al., (1993) *Biochemica et Biphysica Acta* 1173, 121–132 and in European Patent No 0 301 541 and U.S. Pat. No. 5,583,024.

Mutant luciferases may also be used in the methods of the invention (see below).

In a preferred embodiment, the method comprises a further step (b'), carried out after step (b) and before step (c), of adding a reagent to the reaction mixture formed in step (b) which stops the reaction of the kinase with the substrate.

There are a number of acids that are suitable for use as a stop reagent, for example commonly used laboratory acids such as phosphoric acid. Alternatively, high concentrations of EDTA or EGTA may be employed. Luciferase is more resistant to the effects of EDTA/EGTA than other enzymes, and performance in high concentrations of these salts is increased by the use of mutant luciferase enzymes. In addition, any other known buffer for stopping enzyme reactions may be used.

The stopping reagent is preferably phosphoric acid, EDTA or EGTA.

The use of a stopping reagent is particularly advantageous as it allows one to make up and store large numbers of samples prior to testing. This feature is particularly desirable for high throughput applications of the methods of the invention (see below).

The method of this preferred embodiment advantageously comprises a further step (b"), carried out after step (b') and before step (c), of adjusting the pH of the mixture formed in step (b') to a pH at which the luciferase enzyme is active, normally pH 7.0. Preferably, step (b") comprises adding Hepes buffer.

The step of pH adjustment can be avoided by the use of a mutant luciferase which retains the required activity at the pH of the solution following addition of the stopping reagent. It is also useful to employ a luciferase which is active at 30° C., rather than wild type luciferase which is not very active above 25° C. An additional benefit of using thermostable luciferase mutants is that, in addition to their resistance to elevated temperatures, is that key amino acids within the enzyme can be mutated so as to confer other favourable properties that enhance the performance of the enzyme, including resistance to low pH and high salt solutions. These properties are therefore helpful if a stop solution is to be used.

Suitable mutant luciferases can be obtained from Kikkoman Biochemicals, Japan.

Other exemplary mutant luciferases suitable for use in the methods of the invention are disclosed in White et al. (1996) *Biochem J.* 319, 343–350, Squirrel et al. (1997) *J. Defence Science* 2, 292–297, Karp & Oker-Blom (1999) *Biomolecular Engineering* 16,101–104, Branchini et al (1999) *Biochemistry* 38, 13223–13230, Branchini et al. (2000) *Biochemistry* 39, 5433–5440, Tatsumi et al. (1996) *Anal. Biochem.* 243, 176–180, WO 98/46729, WO 96/22376, WO 99/02697, EP 0 449 621 B, U.S. Pat. Nos. 5,330,906, 6,074,859, and WO 95/18853.

Advantageously, step (c) further comprises the following steps carried out after the light intensity measured in step (ii) has reached a substantially constant level:
(iii) adding a reagent that converts ADP to ATP;
(iv) adding a bioluminescent reagent comprising luciferin or a derivative thereof and a luciferase to said reaction mixture of step (iii); and
(v) measuring the intensity of light emitted by the resultant bioluminescent reaction wherein the difference in the intensity of light in step (v) and the steady state intensity of light in step (ii) is a measure of ADP concentration in the reaction mixture of step (ii).

By "substantially constant" we include the meaning that the light intensity does not vary significantly over the same time period as is taken to carry out the light intensity measurements. As a non-limiting example, the term is intended to include the meaning that the rate of change of emitted light intensity is less than 5% per minute, and preferably less than 3% per minute. In any event the person skilled in the art will be able to appreciate whether the level is sufficiently constant to be able to obtain a valid reading of the ATP produced by adding the ADP-converting reagent, not significantly affected by any small change in the ATP baseline.

In an alternative preferred embodiment, steps (b) and (c) are carried out simultaneously.

According to a further aspect, the invention provides a compound identified using a method of the invention.

It will be appreciated by persons skilled in the art that the methods of the invention are suitable for high throughput screening, i.e. screening of large numbers of chemically generated and naturally-derived products for generating leads to pharmaceutical products. In such screening assays, compounds may be put into groups for screening using microtitre plate technologies.

Thus, the methods of the invention can be performed in the small volumes associated with 384 and 1536 well plates, in addition to the 96 well plate format. Under these circumstances, where laboratory robots are used, the assays would be prepared in a large number of plates. The assays could then be carried out using the robots to transport the plates into a luminometer with injectors, and the assay performed as described above.

Another option arises due to the long half-life of the 'glow' of light from the bioluminescence reaction. Once the reaction has plateaued, the emitted light intensity remains substantially constant. This allows for the bioluminescent reagent to be added to the plates in batches, so the plates can be read even 3–4 hours after addition of the reagents.

The invention further provides a kit for use in the method of the second aspect of the invention, comprising:
(a) a bioluminescent reagent comprising luciferin or a derivative thereof and a luciferase, said luciferin or a derivative thereof emitting light in a bioluminescent reaction with the luciferase in the presence of ATP;
(b) a kinase;
(c) a substrate capable of being phosphorylated by said kinase; and
(d) ATP.

The kit conveniently further comprises one or more buffers for reconstituting, diluting or dissolving the bioluminescent reagent, kinase, substrate and/or ATP.

The kit may also further comprise a reagent capable of stopping the reaction of said kinase with said substrate, for example phosphoric acid.

A kit according to the invention may additionally comprise one or more reagent(s) which converts ADP to ATP, such as one which comprises pyruvate kinase and phosphoenol pyruvate.

In a preferred embodiment, the kit of the invention comprises two or more different kinases and their substrates. Thus, there is envisaged a kit suitable for screening compounds to be tested against a plurality of different kinases to determine whether the compound modulates kinase activity and the specificity of such inhibition.

A kit according to the invention may further comprise a multi-well microtitre plate. This term is intended to embrace apparatus which comprises a plurality of reaction vessels or wells linked together in the form of a plate. Each well has a small volume, usually 250 to 300 $\mu$l in a 96 well plate, 60 to 70 $\mu$l in a 384 well plate and 6–8 $\mu$l in a 1536 well plate. At present, the most common plates have 96 wells, but plates having 384 and 1536 wells are known and useful according to the invention. Preferably, the kit comprises a multiwell microtitre plate contains 96 wells or more.

Advantageously, the reagent or reagents in a kit of the invention is or are provided in lyophilised form.

Examples which embody certain aspects of the invention will now be described by way of a non-limiting illustrations which refer to the figures.

EXAMPLES

We have performed a series of experiments to show the effect of protein kinase activity in a cell free system. All the protein kinases and substrates were supplied by Upstate Biotechnology Inc., (UBI) Lake Placid, USA. Any other reagents used in a number of different formulations are shown in appendix 1.

Example 1

Determination of the Activity of JNK-1

The first set of experiments was to determine the activity of JNK-1 after the activation of this enzyme by two other kinases, MEKK1 and MKK4. The assay buffer used to activate the enzymes was made up as a 10 times stock (the formulation is shown in appendix 1). The assay was performed as follows, with an initial preparation of a pre-mix for JNK activation.

The JNK enzyme was used at a stock concentration of 1.234 mg/ml, MEKK1 at 1 mg/ml and MKK4 at 0.28 mg/ml. The activation mixture was added to a polypropylene tube (Sarstedt) with 8.7 µl of JNK, 2.5 µl of MEKK1, 8.4 µl of MKK4, 1 µl of 10 mM ATP (Calbiochem, UK), 1 µl of dithiothreitol (Sigma, UK), 5 µl of 10× assay buffer and 23.4 µl of distilled water. This was incubated overnight at room temperature. To perform the actual assay, the 50 µl of activated concentrate was diluted in 9 mls of JNK assay buffer at the working concentration (i.e. diluted 1:10). The substrate used was GST-c-jun at a concentration of 8.61 mg/ml. Briefly, 12 µl of GST-c-jun was diluted in 1545 µl of working strength assay dilution buffer. Each assay point was performed in triplicate wells of a white, opaque, 96 well microtitre plate (Dynex). To each well was added 15 µl of the substrate mix, followed by 30 µl of the activated JNK enzyme. The reaction was then allowed to proceed at room temperature for one hour. The reaction was then stopped by the addition of 20 µl of 2% (v/v) phosphoric acid (Sigma, UK). To one set of triplicate wells was added 135 µl of Tris-acetate buffer (pH7.75, see appendix 1 for formulation), to a second set of triplicate wells was added 135 µl of 200 mM Hepes buffer (pH 7.75, see appendix 1 for formulation). After this 20 µl of ATP monitoring reagent (see appendix 1 for formulation) was added to each well. The plate was then placed immediately into a Microbeta (RTM) Jet luminometer (Perkin-Elmer Life Sciences), and the light output was determined over a 1 second integral. FIG. 1 shows the drop in light output seen in the presence of the kinase.

Stop Solution

Figure 2:
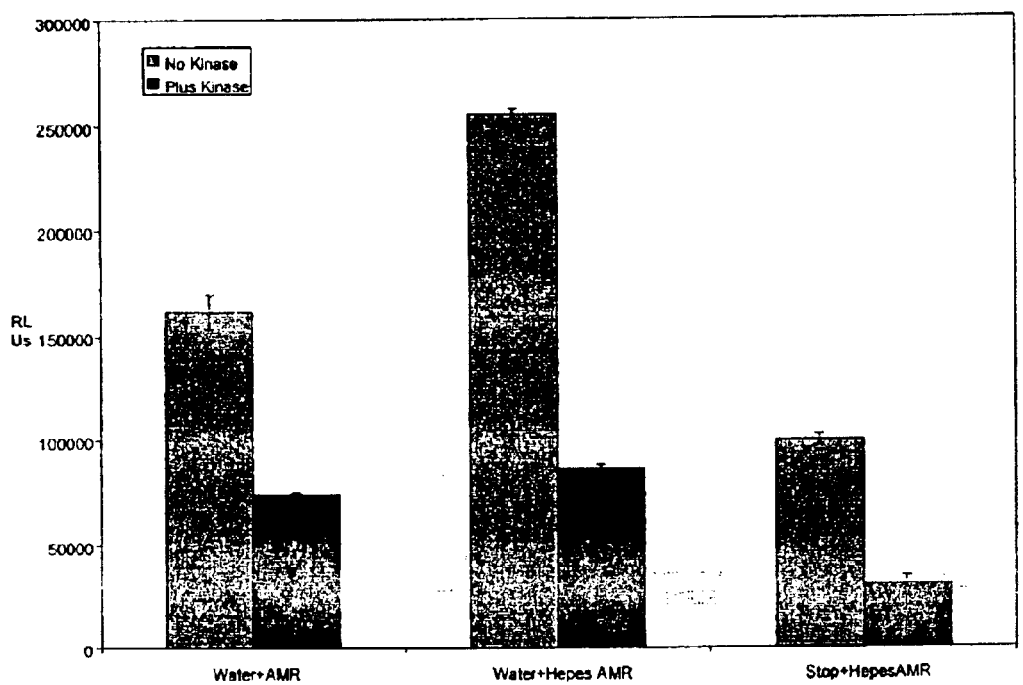
FIG. 2: Shows the effect of Hepes and stop solution on the light output (RLUs) obtained in the presence and absence of activated JNK. The results are expressed as the means of two separate experiments, performed in triplicate±standard deviation (SD). As controls 20 $\mu$l of distilled water was added in place of stop solution.

These experiments were performed with 2% phosphoric acid to halt the kinase reaction at a set time point. A particular advantage of the use of a stop solution, that is, any reagent which can halt the reaction of the kinase and the substrate which it phosphorylates, is that one can make up and store large numbers of samples prior to testing in the methods of the invention. This feature is a particular benefit for high-throughput screening applications. One of the problems with the stop solution is that a reduction in the pH adversely affects the luciferase enzyme, so there must be sufficient buffering capacity when the ATP is measured. In this first series of experiments Hepes proved to be a much better buffer for counteracting the effects of the phosphoric acid. Experiments were performed with increasing concentrations of Hepes, and showed that the 200 mM buffer brought the pH in the well back to pH 7.0 allowing the luciferase-luciferin reaction to proceed without reactivating the kinase. The Tris acetate buffer was less efficient, and while there were still differences in the detected RLUs in the presence of the kinase enzyme, however, they were not as marked as with the Hepes. The results with Hepes showed lower RLUs than without, but this approach did allow for the kinase activity to be controlled prior to being detected using the luciferase-luciferin reaction. As a result of this, most of the following experiments were performed with the 200 mM Hepes, as a dilution buffer, unless otherwise stated. FIG. 2 shows the data from two separate experiments and demonstrates the effects of both the phosphoric acid stop solution and the Hepes buffer.

Skilled persons will appreciate that one may avoid the use of a buffer after addition of the stop solution by using mutant luciferases which are pH and salt stable. It is also desirable to use mutant luciferase which are thermostable at 30° C. rather than wild type luciferase, which is not very active above 25° C. Suitable mutants are available from a variety of sources. For example, pH, salt stable and thermostable mutants can be acquired from Kikkoman Biochemicals, Japan (see above).

Example 2

Determination of the Activity of MAPK-1/ERK-1

To confirm that monitoring of kinase activity by the above method of the invention would proceed with other enzymes that cleave the phosphate from ATP, we looked at a number of other kinases which are important in signal transduction and used as targets in drug discovery.

MAP Kinase-1/ERK-1 activity was investigated in the presence of myelin basic protein as the phospho-acceptor. This enzyme was supplied in the active form from UBI at a stock concentration of 25 µl in 250 µl. Briefly, 10 µl of assay dilution buffer (UBI, see appendix 1 for formulation) was added to triplicate wells of a white-walled 96 well microtitre plate (Dynex).

To this was added 10 µl of MAPK1 and 10 µl of myelin basic protein (UBI, 2 mg/ml), plus 10 µl of ATP cocktail (UBI, for formulation see appendix 1). The plate was sealed and the reaction was allowed to proceed for 10 minutes at 30° C. After this time 110 µl of either assay dilution buffer or Hepes buffer were added to the wells followed by 20 µl of ATP monitoring reagent reconstituted in 200 mM Hepes buffer. The results showed a reduction in light output with this enzyme in the presence of its substrate. With the UBI buffer there was a drop in RLUs from 77367 to 35578, with the Hepes buffer there was a reduction from 91256 to 73424.

Detection Based on Increase in ADP

Figure 3:
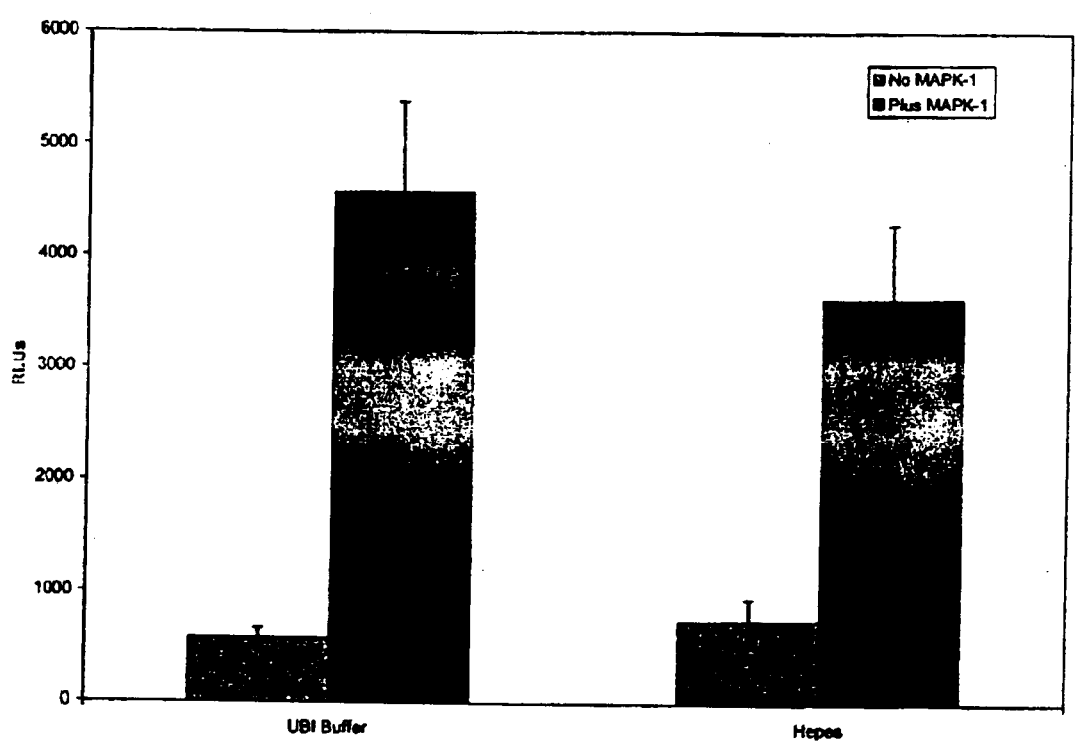
FIG. 3: Shows the effect of MAPK-1/ERK-1 on an increase in ADP. The data are presented as the difference in RLUs, pre and post addition of converting reagent. The results represent the means of 6 different replicates for each condition±SD.

With this experiment we also determined whether it would be possible to detect any resultant increase in ADP by the conversion of ADP to ATP, through the addition of 20 µl of an ADP converting reagent containing pyruvate kinase (for formulation see appendix 1). To determine the amount of ADP, a reading was taken after the initial ATP light signal had been allowed to decay for 10 minutes. The converting reagent was then added and a further reading taken after 5 minutes. All of these readings were integrals taken after 1 second using the Microbeta (RTM) Jet (Perkin-Elmer Life Sciences). The amount of ADP present correlated with the difference in light output between the final reading and the reading taken prior to the addition of converting reagent. The data showed that it was possible to determine an increase in ADP, as shown in FIG. 3.

Example 3

Determination of the Activity of MAPK-2/ERK-2

The above protocol was also used for determining the effect of MAPK-2/ERK-2 in the presence of the same substrate, myelin basic protein. The MAPK-2 was supplied by UBI at a concentration of 2.5 µg of enzyme in 25 µl of buffer (for formulation see appendix 1), with a specific activity of 662.5 U/mg, where 1U=1 nmole of phosphate incorporated into myelin basic protein. This enzyme was compared with the inactive form, also supplied by UBI at a concentration of 12.5 µg in 50 µl. Both enzymes were diluted in UBI assay dilution buffer to allow for the addition of 25 ng of protein in 10 µl to each well. The myelin basic protein was added as described in the above example, and 200 mM Hepes was used as the buffer added to the wells prior to the addition of the ATP monitoring reagent. The assay was performed in triplicate wells and showed RLUs of 10075±339 for the inactive enzyme, which was very similar to the light output from the no enzyme controls (11440±1372). The RLUs for the active enzyme showed a drop in ATP, after the 10 minutes incubation, to 7008±430. It was also possible to detect an increase in RLUs after addition of ADP converting reagent in the active sample of 5272, compared with 441 with the inactive enzyme.

Example 4

Effect of Kinase Concentration on Reduction in ATP

Figure 4:
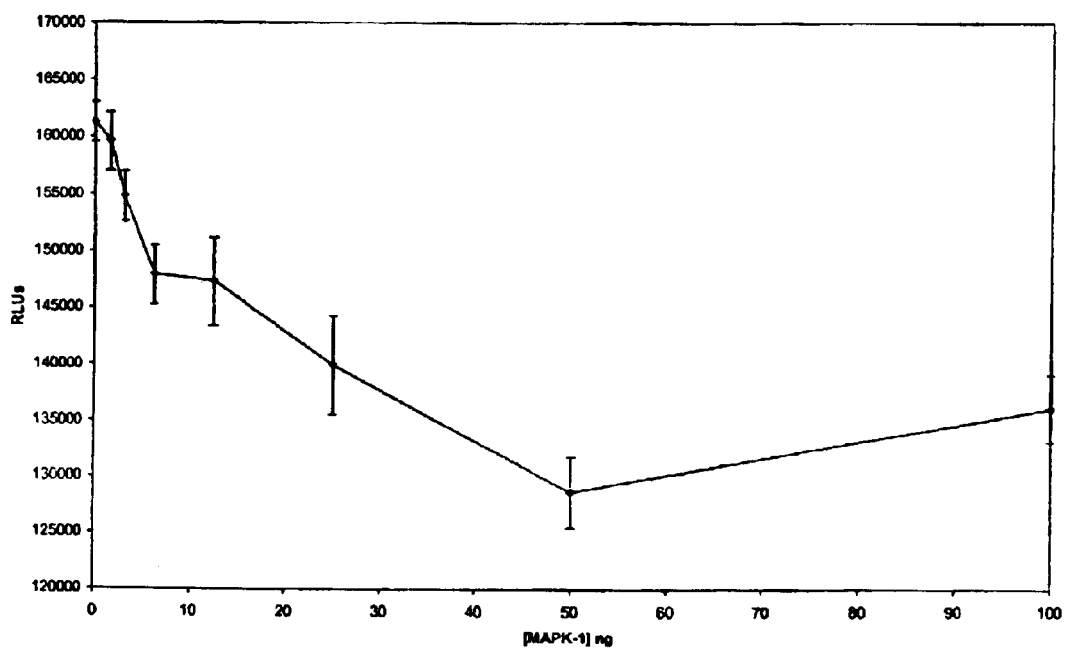
FIG. 4: Shows the effect of increasing concentrations of MAPK-1 on the drop in light output. The results are expressed as the means of three separate experiments performed in triplicate±SEM.

To determine whether there was a concentration dependent effect of kinase activity on reduction in ATP, MAPK-1 was used at concentrations ranging from 1.56 ng/10 µl to 100 ng/10 µl, with serial doubling dilutions from the highest concentrations. The concentration of myelin basic protein used was the same as in the previous experiments. The assays were performed as in the previous two experiments, i.e. using UBI reagents, but with the addition of 110 µl of 200 mM Hepes buffer prior to determination of ATP readings. The results showed a concentration dependent reduction in ATP levels detected with increasing concentrations of the MAPK-1. There was no effect of the enzyme when 1.56 ng was added to each well, however, there was a significant effect at concentrations of 3.13 ng and above (see FIG. 4).

Example 5

Effect of ATP Concentration on Light Decay: Influence of Buffer Type

Figure 5:
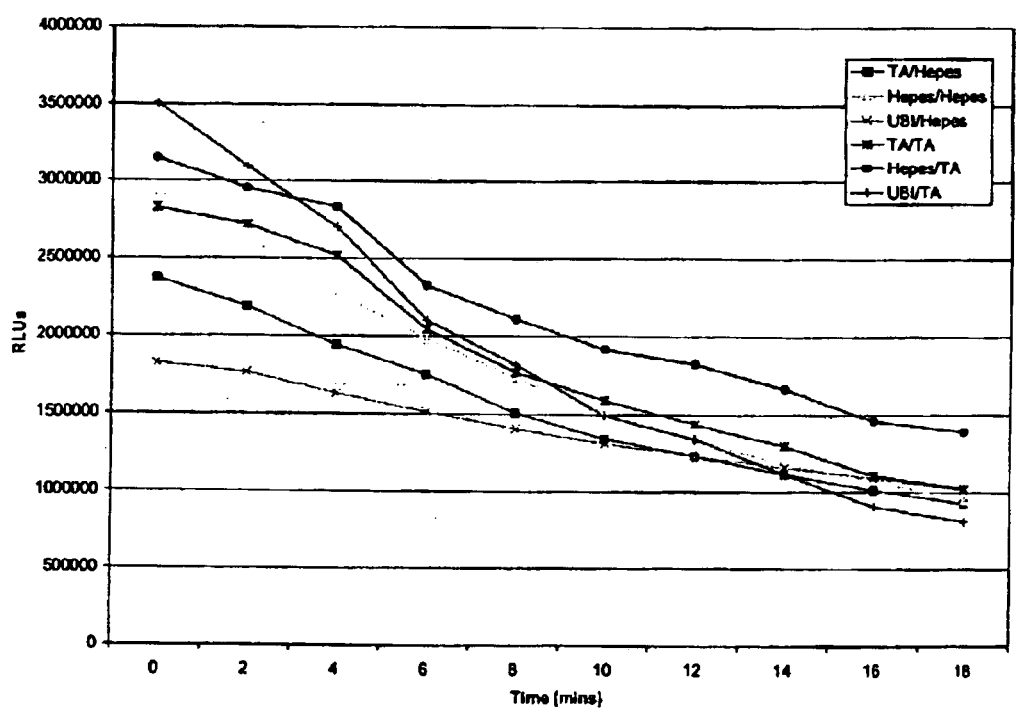
FIG. 5: Shows the initial light output and subsequent signal decay observed with ATP monitoring reagent and 12 $\mu$M ATP in different buffering conditions. The results shown are from one representative experiment.

The luciferase enzyme itself is an ATPase that converts ATP to AMP and inorganic phosphate. After the initial increase in light output as a result of the luciferin-luciferase reaction, the light signal begins to decay over time. We examined the light decay with increasing concentrations of ATP up to the 200 µM used in the above experiments. The ATP standards (Sigma, UK) were diluted at serial doubling dilutions from 200 µM down to 3.125 µM per 10 µl added to each well. The standards were diluted in three different buffers, assay dilution buffer from UBI, Tris acetate buffer (pH 7.75) and 200 mM Hepes pH 7.7. 10 µl of the standards, plus a no ATP buffer control, were added in to triplicate wells of the opaque-white 96 well microtitre plates. The experiments were run with duplicate plates, one where 140 µl of the Tris-acetate buffer was added to all wells, and the other where the same volume of 200 mM Hepes buffer. Immediately after the addition of these reagents 20 µl of ATP monitoring reagent was added to all wells. The plate was then placed in a Berthold (RTM) Detection Systems MPL2 luminometer, and the program was set to take 1 second integral readings for each well every 2 minutes. The FIG. 5 graph shows the initial light output (at time 0) and the decay in the light signal observed with the different buffer conditions and the 200 µM stock ATP (final concentration in the well of 12 µM).

Example 6

Figure 6:
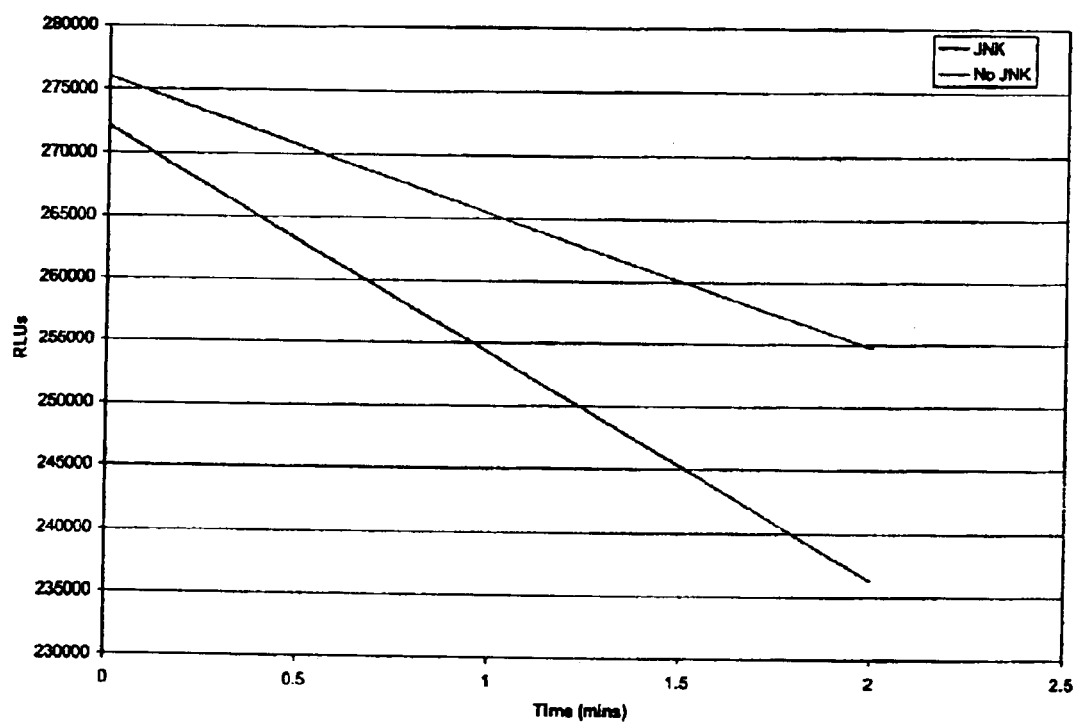
FIG. 6: Shows the effect of JNK-2 activity on the signal decay measured over the first two minutes, in the presence of ATP monitoring reagent. The results are from one experiment, representative of three. The assays were performed in triplicate wells of a white 96 well microtitre plate.

Effect of Luciferin-Luciferase (ADR) Reagent on Kinase Assay: Detection of Kinase Activity as a Drop in Light Signal Experiments were also carried out to investigate the effect of performing the kinase assay in the presence of luciferin-luciferase reagent (ADR), and its effect upon the rate of signal decay. The enzyme used was JNK-2 (Upstate Biotechnology Inc, USA) at 1 µg per 10 µl added to each well, the c-jun (1–169)-GST substrate (Upstate Biotechnology Inc, USA) was also added at the same concentration. Into each well was added 10 µl of 200 µM ATP standard and 10 µl of Hepes buffer (200 mM). Into control wells the 10 µl of enzyme was replaced by 10 µl of Hepes buffer, once all the active reagents were in the wells and an additional 120 µl Hepes dilution buffer had been added, then 20 µl of ADR was added and the signal decay monitored every 20 seconds over a 2 minute period, using a Berthold (RTM) Detection Systems MPL-2 luminometer. A 1 second integral reading was taken at each time point. The data showed an increase in the rate of signal decay in the presence of the JNK-2 enzyme, as shown in FIG. 6. This shows that kinase activity can also be detected as an accelerated drop in light signal, in the absence of a stop solution.

Example 7

Comparison of Active and Inactive Forms of a Kinase

Figure 7:
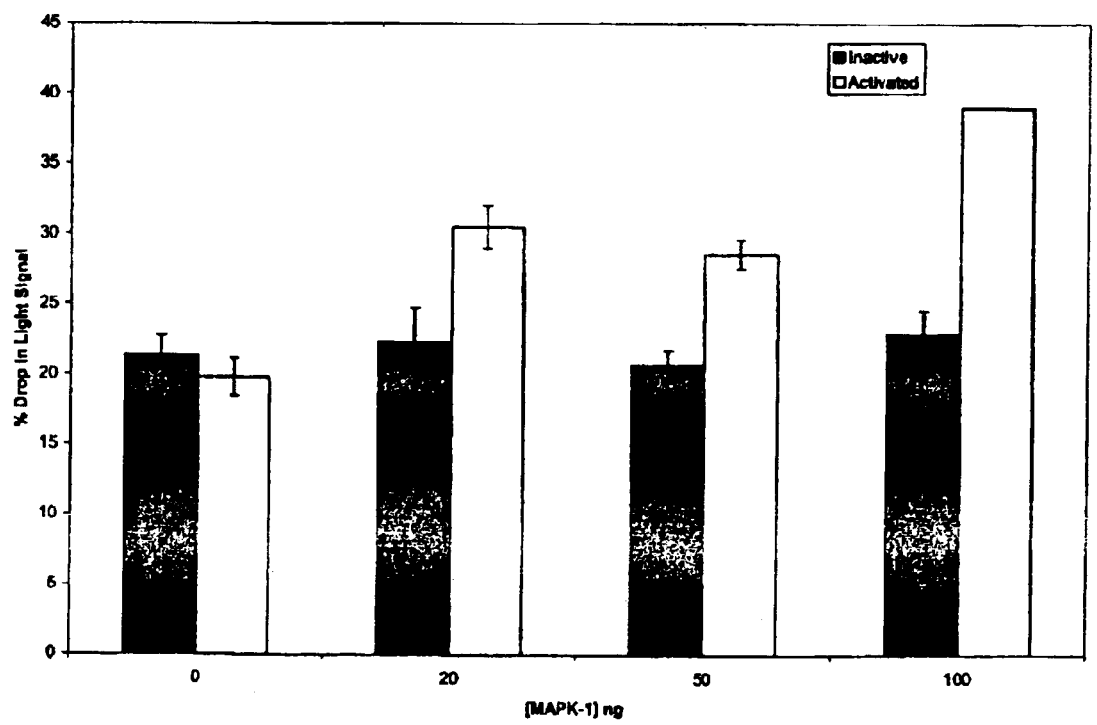
FIG. 7: Shows the effect of increasing concentrations of MAPK-1 on the decay in light signal. This experiment also compared the effect of the activated form of the enzyme versus the inactive form. The results are expressed as the means of triplicate experiments±SD.

We also compared activated and inactive forms of MAPK-1 and MAPK-2, and showed reduced kinase activity with the inactive forms of the enzymes, although in some cases there did appear to be a certain amount of autophosphorylation, this was not significantly different from the no enzyme controls. A concentration curve for inactive MAPK-1 versus the activated form, showed clearly how the kinase activity of the enzyme reduced the amount of ATP and hence increased the signal decay. The experiment was performed as detailed in Example 3, however in this case the kinetics of the reaction were investigated over the first 6 minutes of the reaction. From FIG. 7, it can be seen that at 100 ng of MAPK-1 per 10µl (588 ng/ml final concentration) gave a significant increase in the % signal decay by 6 minutes. The assay was performed in triplicate in 3 different experiments. As soon as the ADR had been added the plate was read for 1-second integrals every minute for 6 minutes, using a Labsystems Luminoskan (RTM) luminometer.

A similar effect was also seen with the phosphorylation of MAPK-2 by MEK-1. In this series of experiments the MEK-1 was used at final concentrations in the well of 75 µg/ml through to 375 µg/ml by the addition of 1–5 µl of stock enzyme at 5U/50 µl. The activity quoted from Upstate Biotechnology Inc was 7850 U/mg where 1 unit will maximally activate 1 unit of inactive MAPK-2. The inactive MAPK-2 was added to each well in 10 µl volumes to give a final concentration of 5.88 mg/ml. Again, in the presence of 200 µM ATP and Hepes buffer, there was a concentration dependent increase in the signal decay from 14% in the control to 36% for the highest concentration used.

Example 8

Effect of Different Kinase Buffers

Figure 8:
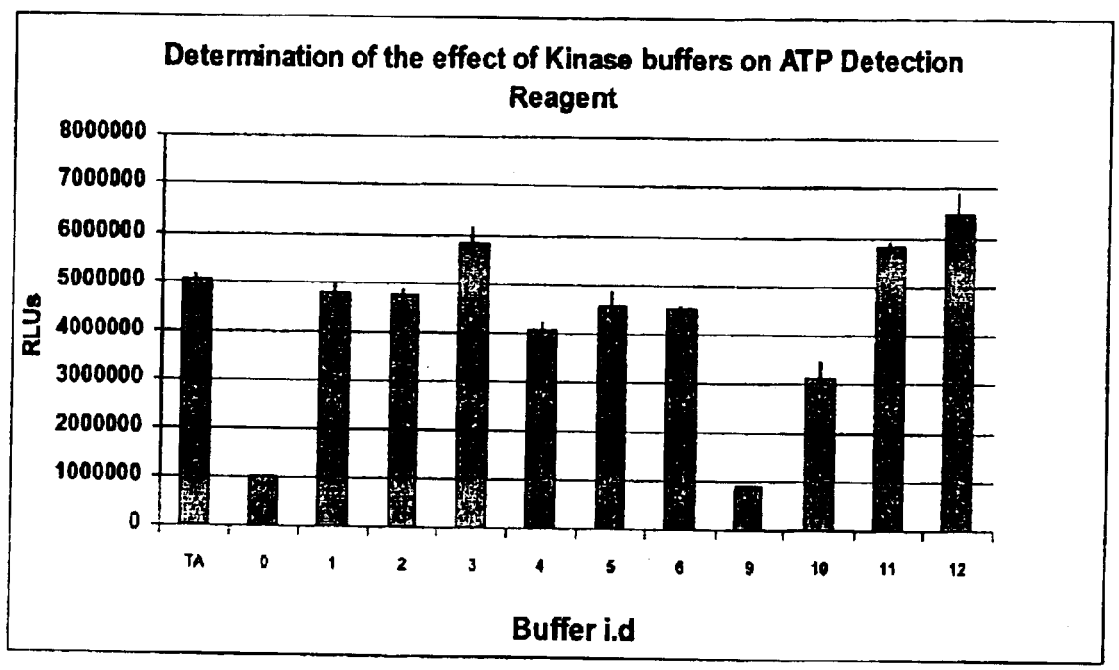
FIG. 8: Shows the effect of different kinase buffers on light output (RLUs) with 1 $\mu$M ATP. The data are shown as the means of 6 replicate wells±SD. See Table 1 for buffer details.

In the literature there are a number of different reaction buffers that are used to perform kinase assays, we therefore decided to test the ATP detection reagent with these buffers, to ensure that the assay would perform irrespective of the constituents of the buffer. The reason these buffers are used is to supply optimal conditions for the kinase reaction in the presence of the ATP and protein/peptide substrates. FIG. 8 shows the effect of 13 different buffers commonly used in protein kinase assays. The buffer constituents are shown in Table 1.

TABLE 1

| Buffer i.d. | Buffer contents | Used for Kinases |
|---|---|---|
| 0 | 100 mM Tris Hel pH 7.4 containing 20 mM DTT, 20 mM $MnCl_2$, 10% Glycerol and 0.004% Brij-35 | SBE Mix (Astrazeneca) |
| 1 | 8 mM MOPs pH 7.0 containing 0.2 mM EDTA | GSK3β, S6k1, MAPKAP-K1b/RSK2, PKA, CHK1 CHK2, MSK1 and SGK |
| 2 | 50 mM Tris-Hcl pH 7.75 containing 0.05% 2-Mercaptoethanol | PKBα |
| 3 | 25 mM Tris-Hcl pH 7.5 containing 0.1 mM EGTA | ERK-2 SAPk2α/p38, SAPk2b/p38/p32, SAPk3 and SAPk4 |
| 4 | 50 mM Sodium β glycerophosphate pH7.5 containing 0.1 mM EGTA | MAPKAP-K2 and PRAK |
| 5 | 50 mM Tris-Hcl pH 7.5 containing 0.1 mM EGTA and 0.1% 2-Mercaptoethanol. | JNK-1, ROCKII and PRK-2 |
| 6 | 50 mM Hepes pH 7.4 containing 1 mM DTT, 0.02% Brij-35, and 0.2 mM AMP. | AMPK Respiratory |
| 7 | 20 mM Hepes pH 7.4 containing 0.03% Triton X-100, 0.1 mM $Cacl_2$, 0.1 mg · ml phosphatidylserine and 10 μg · ml 1,2-dioleoyl-sn-glycerol. | PKCα |
| 8 | 20 mM Hepes pH 7.4 containing 0.03% Triton X-100, 0.1 mM EGTA, 0.1 mg · ml phosphatidylserine. 10 μg · ml 1,2-dioleoyl-sn-glycerol | PKCδ |
| 9 | 20 mM Hepes pH 7.6 containing 150 mM NaCl, 0.1 mM EDTA, 5 mM DTT and 0.1% Triton X-100 | CK2 |
| 10 | 50 mM Tris-Hcl pH 7.5 containing sodium β-glycerophosphate, and 0.04 mM $Cacl_2$ | PHK |
| 11 | 25 mM Tris-Hcl pH 7.5 containing 0.1 mM EGTA, 0.1% 2-Mercaptoethanol and 0.01% Brij-35 | ERK2 |
| 12 | 50 mM Tris-Hcl pH 7.5 containing 0.1% 2-Mercaptoethanol | PDK-1 |
| 13 | 50 mM Tris-Hcl pH 7.5 containing 0.1 mM $CaCl_2$, 10 units per ml calmodulin and 0.1% 2 Mercaptoethanol. | MLCK |
| 14 | 50 mM Tris-Hcl pH 7.5 containing 0.1 mM EGTA, 0.1 mM $Na_4Vo_3$ | LCK 14 |

The ATP was diluted in each of the buffers and 100 μl was added to each well of a 96 well microtitre plate, 20 μl of ATP detection reagent was added to the wells, and the light output was detected after a 1 second integral reading using a Berthold (RTM) Detection Systems Orion Luminometer.

The results in FIG. 8 show that buffers 0 and 9 compromise the light output, however the sensitivity of the assay was unaffected. These assays are normally performed with ATP concentrations from tens to hundreds of micromolar, i.e. greater than the 1 μM concentration used in this example, where a significant light output was still detectable with the buffers that reduced the signal.

Example 9

Use of Tris Acetate Buffer in Bioluminescence Assay

We have compared the performance of the bioluminescent assay in Tris buffer as well as Hepes. We have shown that it is possible to reconstitute the ATP Detection Reagent in Tris Acetate Buffer at pH 7.75. However, when using an acid stop solution, for example phosphoric acid, it is preferable to use the Hepes buffer reconstitution system described above.

The assays were performed using a number of different kinases and substrates. The experiments were carried out using methods similar to that described for Hepes buffer. The assays were performed in 100 μl volumes in wells of a 96 well microtitre plate, the appropriate concentrations of each enzyme and substrate were added to the wells in the most suitable reaction buffer for that enzyme. The reaction was then initiated by the addition of ATP at the appropriate concentration, the reaction was allowed to proceed at 30° C. for 10 minutes prior to addition of 20 μl of ATP detection reagent (reconstituted in Tris acetate buffer), light output was detected over a 1 second integral. In the following examples, the ATP detection reagent was reconstituted in Tris-acetate buffer pH 7.75, rather than a Hepes.

JNK2α2 with ATF-2 and c-Jun as Substrates

This enzyme was tested with both the ATF-2 and c-Jun substrate peptides from Upstate Discovery.

| Assay Buffer: | 100 mM Tris-HCl pH 7.4 |
|---|---|
| | 20 mM Dithiothreitol |
| | 20 mM $MgCl_2$ |
| | 10% glycerol |
| | 0.004% Brij 35 |

Time course experiments were performed in 100 μl (or 200 μl) volumes in clear plastic test tubes. The reaction was carried out in either a 30° C. waterbath or in an incubator.

Upstate Discovery recommend use of the ATF-2 substrate at 5 μg per assay point and the JNK2α2 at 20 mU per assay point.

Stock ATF-2 (LB018LFp107) at 4.3 mg/ml in 10 μl aliquots (43 μg in 10 μl). The substrate was diluted 1:8 from stock and then 10 μl added to the tube to give a final amount in the reaction mixture of 5.38 μg.

Stock JNK2α2 (LB021SDp81) is at 77U/mg (100U/ml) and 1.3 mg/ml and aliquoted into 10 μl aliquots (1U). Concentration curves were performed with the addition of 5 μl of neat enzyme stock (50 mU), 5 μl of 1:2 (25 mU), 1:4 (12.5 mU) and 1:8 (6.25 mU) per 100 μl of final reaction volume.

Stock ATP at 1M in 10 μl aliquots. The ATP was diluted 1:40 with Tris-HCl buffer (addition of 390 μl) and then a further 1:100 to give a working solution of 250 μM. Then 10 μl was added to each 100 μl of final reaction volume, this gave a final concentration in the tubes of 25 μM.

| The tubes therefore contained: | 10 μl substrate |
|---|---|
| | 5 μl enzyme |
| | 10 μl ATP |
| | 75 μl assay buffer |

To determine kinase activity 20 μl samples were removed from the tubes at 5 minute intervals and added to the wells of a 96 well white opaque microtitre plate. Then 20 μl of ADR reconstituted in Tris-Ac buffer was added to the wells, and the plate read in the luminometer over a 1 second integral.

To determine reproducibility a larger volume was prepared and triplicate samples taken over reduced time points.

Figure 9:
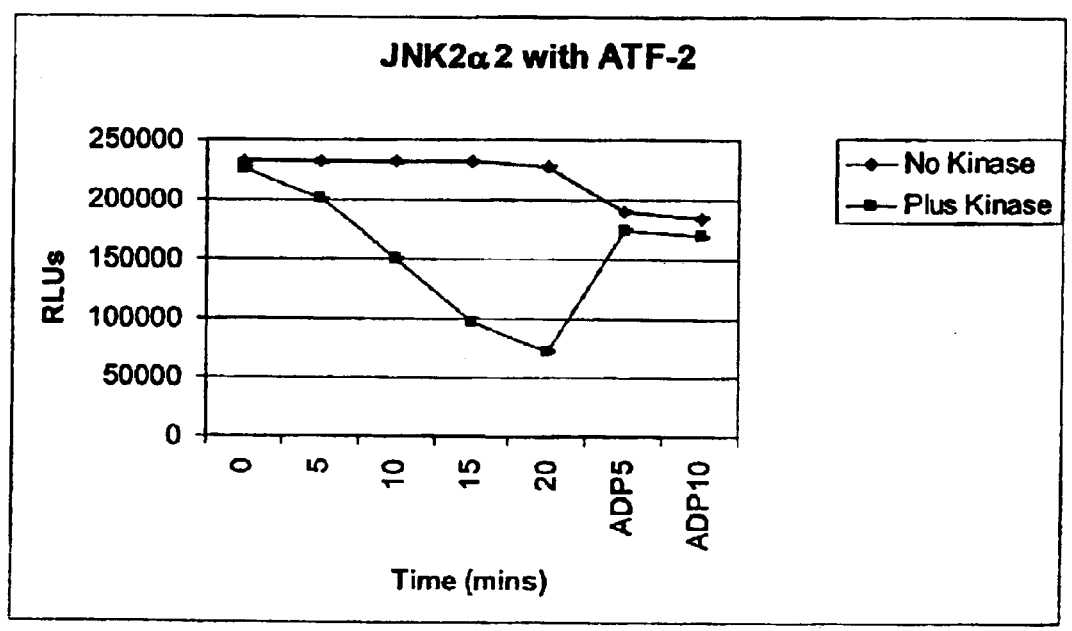
FIG. 9: Shows the time course for the reduction in light output over time as a result of JNK2$\alpha$2 kinase activity with ATF-2 as substrate. ADP detection was performed to act as a control confirming cleavage of the phosphate group from ATP. JNK2$\alpha$2 was used at 50 mU and ATF-2 at 5.38 $\mu$g.

FIG. 9 shows the drop in light output with time in the presence of enzyme and substrate compared with the substrate only control.

FIG. 9 also shows the effect of adding ADP converting reagent (20 μl), this converted the ADP formed as a result of kinase activity back to ATP, for detection with the ATP detection reagent. The drop in light signal after pipetting of the ADP converting reagent was due to a drop in pH in the well after addition. FIG. 9 clearly shows a marked drop in light output in the presence of enzyme and substrate compared with the no enzyme control.

Figure 10:
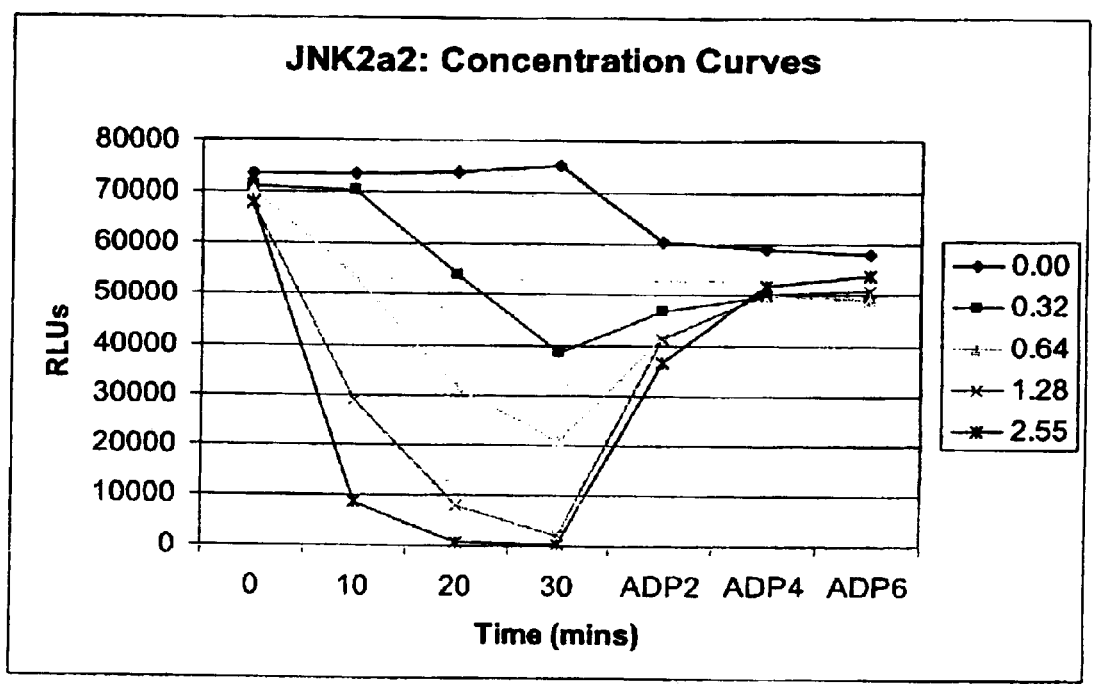
FIG. 10: Shows a JNK2$\alpha$2 concentration curve of the reduction in ATP with time at 30° C. as an indication of kinase activity. ADP converting reagent was added to confirm the presence of ADP in the reaction mixture.

As described in the above methods, the assay was repeated with decreasing concentrations of JNK2α2, against the same ATP and peptide concentrations. FIG. 10 shows the data obtained with 2.55 μM (50 mU) down to 320 nM JNK2α2.

In addition to ATF-2 we also studied another JNK substrate, namely the peptide c-Jun. For determining JNK2α2 activity with the c-Jun peptide the experiments were performed using the same protocol as above, but with the addition of 10 μl of c-Jun rather than the ATF-2.

Stock c-Jun (LB023JTp72) at 4.83 mg/ml in 805 μl in 10 μl=48.3 μg, to use approximately the same amount of peptide as ATF-2 again dilute 1:9 and then add 10 μl per tube.

Figure 11:
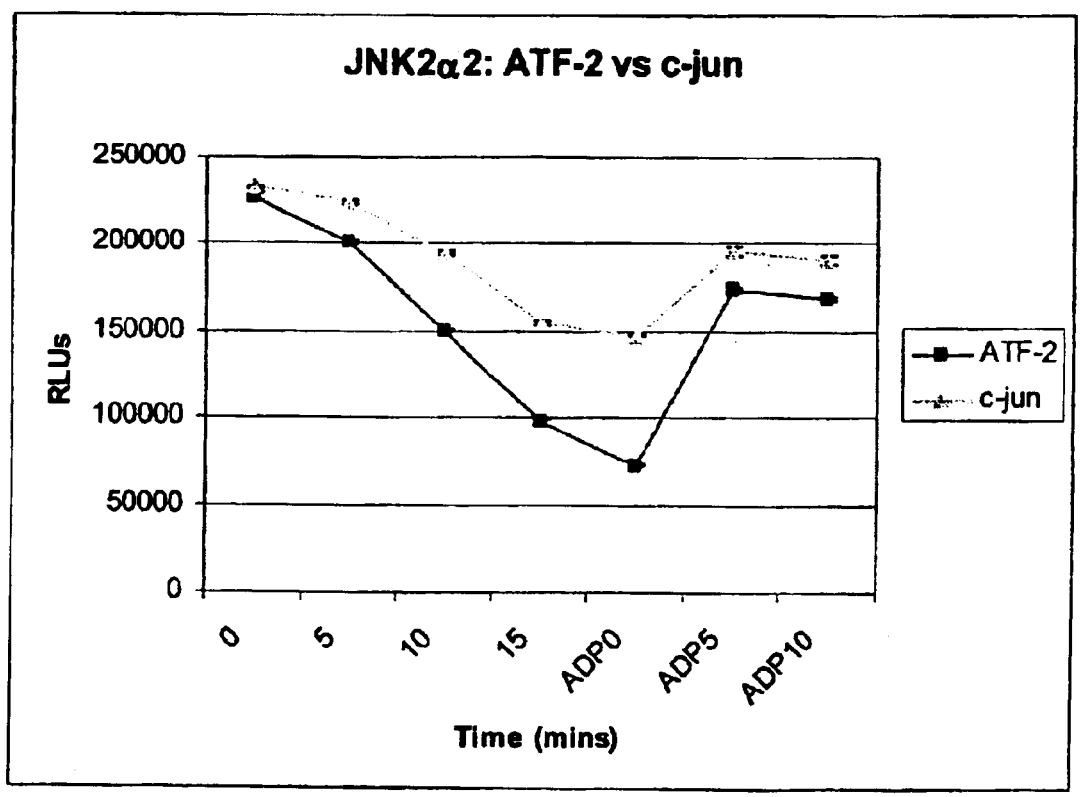
FIG. 11: Shows a comparison of the drop in light signal using JNK2$\alpha$2 with c-Jun and ATF-2 as substrates.

FIG. 11 compares the drop in ATP as a result of kinase activity when the two different substrates were compared. The data confirmed information received from Upstate Discovery that the ATF-2 was a more efficient substrate than the c-Jun, for JNK2α2 activity.

SAPK-3 and Myelin Basic Protein

SAPK3 is a member of the mitogen activated protein kinase (MAPK) family, which can be activated by a variety of extracellular agonists. These stress activated protein kinases can utilise myelin basic protein (MBP) as the phospho-acceptor in kinase reactions. We have shown that this kinase activity can be determined with ADP detection reagent reconstituted in Tris acetate buffer (pH 7.75) in addition to Hepes buffer. The assays were performed as follows.

This assay was performed using the same buffer as for MAPK-2/ERK-2, with a 30° C. incubation. ATP was used at the same concentration as for JNK2α2.

| Assay Buffer: | 25 mM Tris-HCl pH 7.5 |
| --- | --- |
| | 10 mM Mg acetate |
| | 0.1 mM EGTA |

As with the previous enzyme the assay was set up in tubes in order to perform a time course. After the kinase reaction was completed 20 μl of reaction mixture was placed in the wells of a 96 well opaque white microplate, followed by addition of 20 μl of ATP detection reagent. The light output was again determined over a 1 second integral.

Tubes contained: 10 μl enzyme, 10 μl substrate, 10 μl ATP and 70 μl assay buffer.

SAPK3 stock solution (LB012SDp174; 220 μl) was provided at a concentration of 1.55 mg/ml and 87.3U/mg. The enzyme was aliquoted into 10 μl aliquots (15.5 μg). The enzyme was then diluted 1:3 (=5.17 μg/10 μl). For enzyme concentration curves the enzyme was diluted a further 1:5 (1.03 μg) and 1:10 (0.52 μg). The assay was performed by the addition of 10 μl per 100 μl final reaction volume. The final enzyme concentrations were 0, 0.517, 1.03 and 5.17 μg/ml (corresponding to nanomolar concentrations of 0, 72.8, 145.6 and 728.0 nM, respectively; see legend to FIG. 12).

MBP from Calbiochem (0.5 mg/ml) used 10 μl of the neat stock per 100 μl final reaction volume (2.72 μM final concentration).

Figure 12:
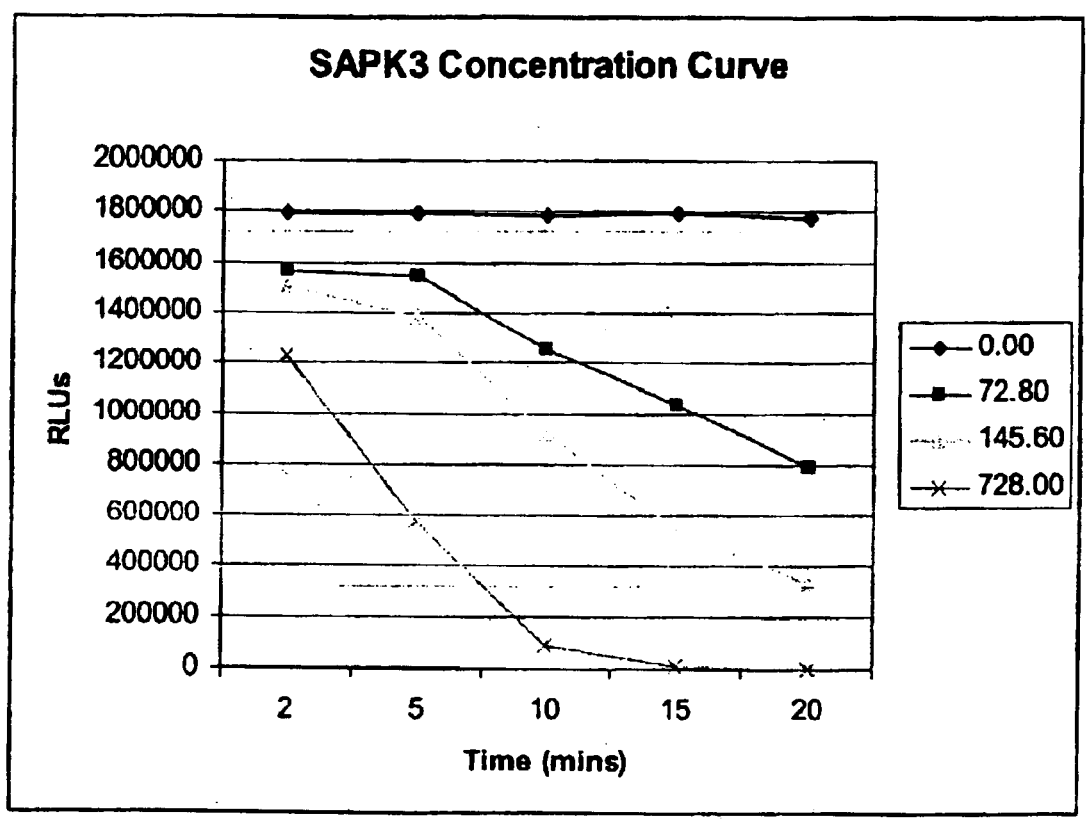
FIG. 12: Shows a SAPK3 concentration curve with a concentration dependent drop in light signal. The SAPK3 concentrations are shown as nanomolar.

Results of the SAPK3/MBP experiment are shown in FIG. 12, in which a concentration dependent drop in ATP (as measured by light output) is evident.

SAPK4 and Myelin Basic Protein

The above experiment was also repeated with SAPK4 and MBP. These assays were performed using the same assay buffer as for MAPK2/ERK-2 and SAPK3.

Stock SAPK4 (LB012SDp176) at 1.64 mg/ml and 144.1U/mg in 127 μl. This was aliquoted into 5 μl samples (8.2 μg/aliquot). To generate a working stock the enzyme was diluted 1:4 (2.05 μg/5 μl), then further 1:5 (410 ng/5 μl) and 1:10 (205 ng/5 μl). Then 5 μl was added to each tube, this gave final concentrations in the tubes, for a 100 μl reaction volume of 0, 0.103, 0.205 and 1.25 μg/ml (corresponding nanomolar concentrations are shown in the FIG. 13).

Stock MBP, Life Technologies at 2.5 mg/ml. 10 μl was added to each 100 μl final reaction volume (250 μg/ml or 13.6 μM).

Figure 13:
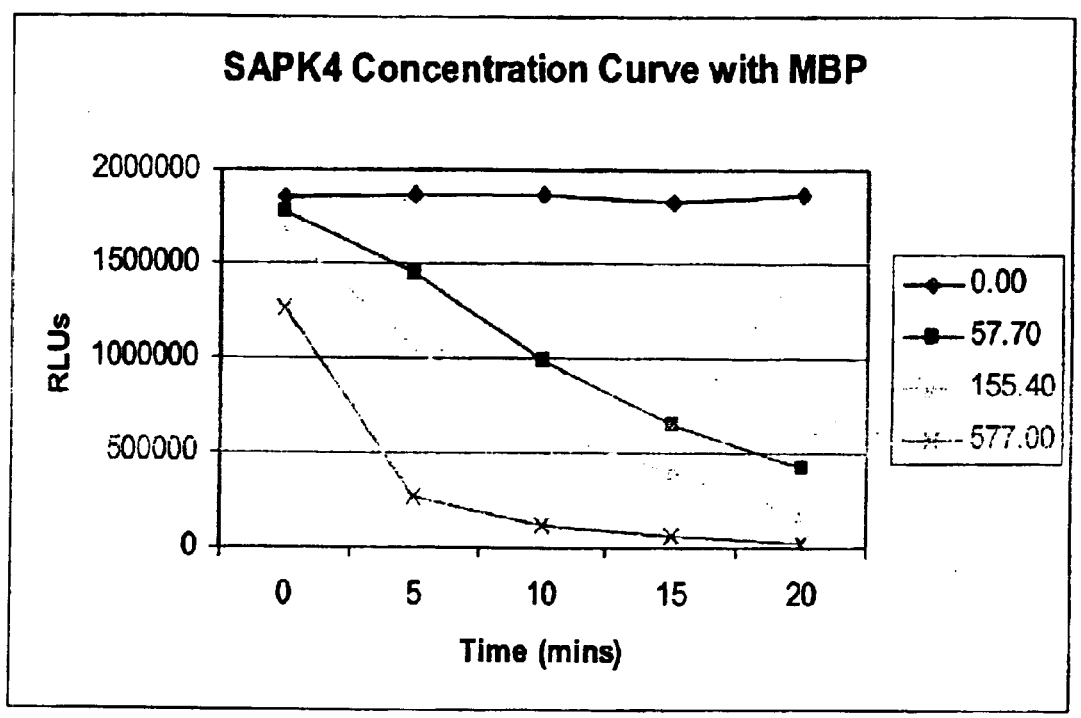
FIG. 13: Shows the concentration dependent effect of SAPK4 on reduced light output (with MBP substrate). The SAPK4 concentrations are shown as nanomolar.

The higher concentration of MBP showed a rapid decrease in the light signal at time 0, this was in fact approximately 2 minutes after the addition of the reagents, as it took this long to remove samples from the tubes, plate them out and then add the ATP detection reagent (see FIG. 13).

The work performed with the SAP kinases also showed that it was possible to use MBP from a number of different suppliers (although the performance of the assay was found to depend upon the quality of the protein provided).

These data confirm that Tris-acetate buffer could be used for ATP detection reagent reconstitution as well as the Hepes buffer described previously.

Example 10

Effect of ATP Concentration

All of the above assays were performed with ATP at a final concentration of 25 μM. We went on to investigate whether the bioluminescent system could detect kinase activity with higher and lower ATP concentrations. The assays were performed with the same buffers as described above, and with the same volumes. However, in the following examples the experiments were performed in the wells of white-walled 96 well microtitre plates, rather than in tubes. After 30 minutes at 30° C., the plates were removed from the incubator and 20 μl of ATP detection reagent was added to each well and the light out put read over a 1 second integral.

JNK2α2

Figure 14:
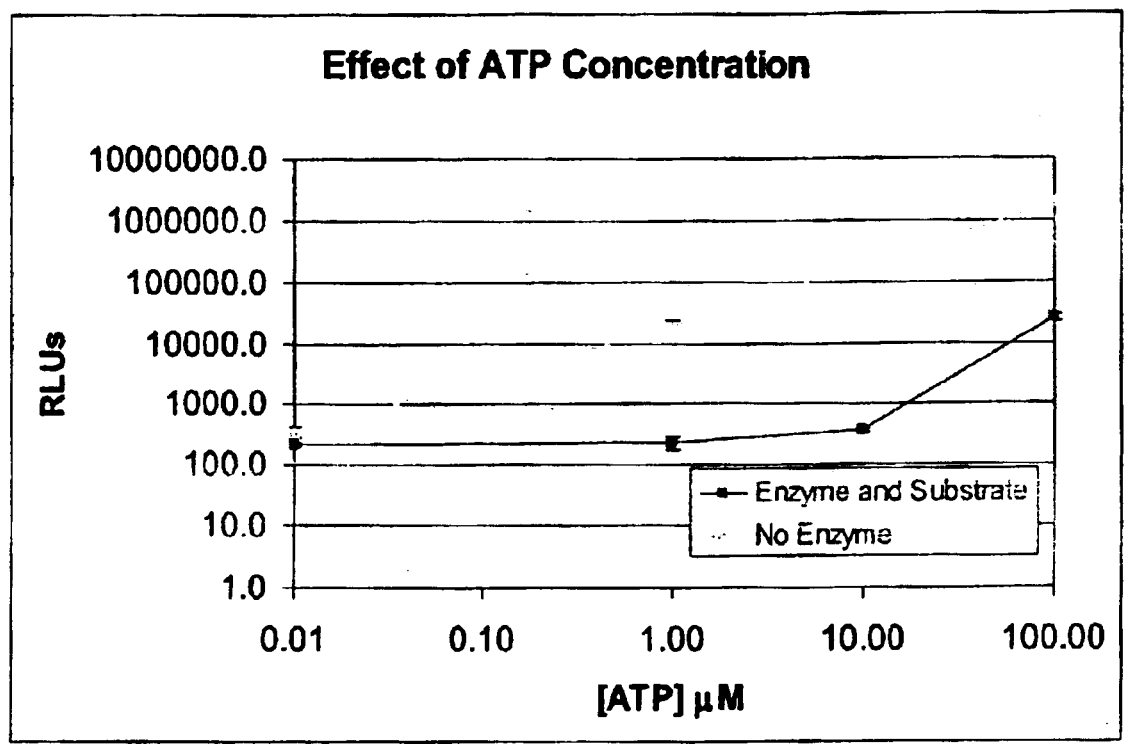
FIG. 14: Shows the effect of increasing concentrations of ATP detection of JNK2$\alpha$2 activity in the presence of ATF-2 as substrate. The results are the means of triplicate wells±SD.

FIG. 14 shows the data obtained with ATP at 3 different final concentrations 1, 10 and 100 μM (results are shown as means of triplicate wells±SD). The substrate used was ATF-2 at a final concentration of 2.11 μM, with enzyme at 1.25 μM. The assay buffer was the same as that described for JNK2α2 above.

SAPK3

Figure 15:
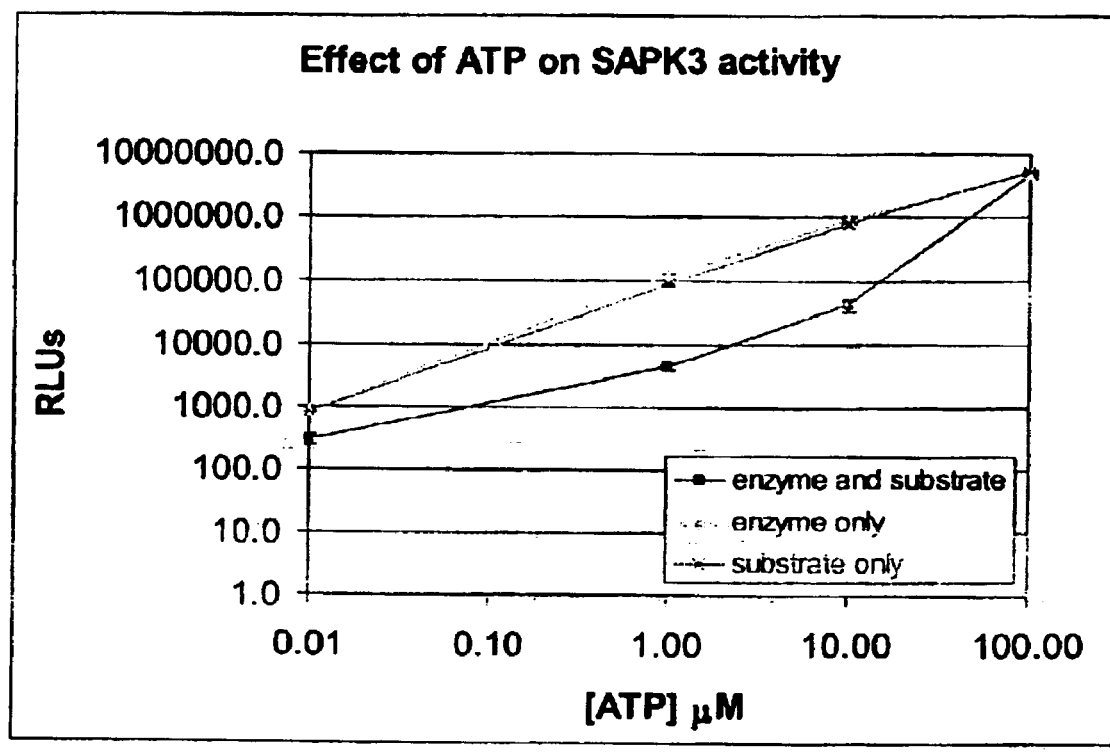
FIG. 15: Shows the effect of increasing ATP concentrations on SAPK3 activity in the presence of MBP as substrate. The results are shown as the means of triplicate wells±SD.

The ATP concentration curve experiments were repeated with SAPK3 and MBP as substrate. FIG. 15 shows the effect of different ATP concentrations on the change in light output (results are shown as the means of triplicate wells±SD). The SAPK3 was used at a concentration of 728 nM, with myelin basic protein (MBP) at a final concentration of 2.72 μM in the wells. At 100 μM there was an effect of the enzyme in the presence of the substrate where the light signal dropped by 693,234 RLUs, from 5,267,900±133,688 to 4,574, 666±283,204. This was a significant decrease in RLUs and indicated that the amount of enzyme and substrate was limiting at this high concentration of ATP.

The differences in RLUs correlate directly with ATP concentrations this drop in light out put relates to the amount of ATP dephosphorylated by the SAPK3. This is further demonstrated in FIG. 16, where the differences in RLUs are shown, which indicates that the same amount of ATP was consumed at 100 μM ATP as 10 μM.

Figure 16:
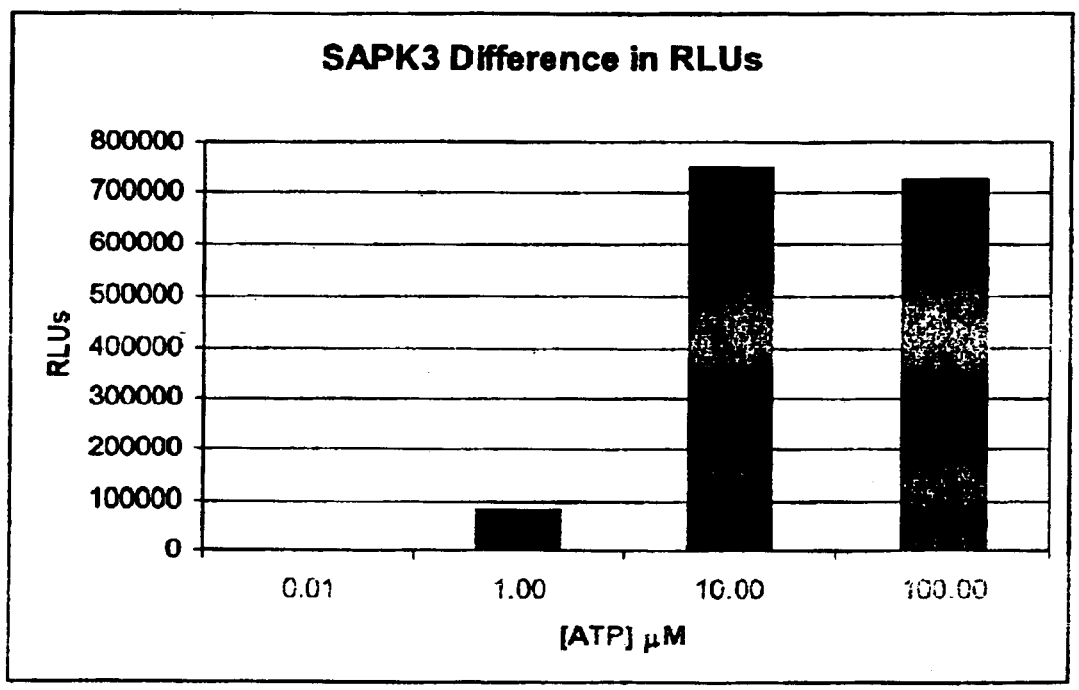
FIG. 16: Shows the reduction in RLUs in the presence of increasing concentrations of ATP for SAPK3 and MBP. SAPK3 was used at 728 nM with MBP at a final concentration of 100 $\mu$g/ml.

Although it is not clear from FIG. 16, there was also a significant difference in RLUs with the lowest concentration of ATP used, where the RLUs dropped from 818±18 to 300±17 (means±SD).

Example 11

Assay Performance in 384 Well Microtitre Plates

The time course experiments described above confirmed that it was possible to perform the assay in tubes in large volumes, and then at each time point sample 20 μl for addition to a white opaque microtitre plate (96 wells), with light output being measured after the addition of 20 μl of ATP detection reagent. We have also shown that it is possible to perform the assay in 100 μl volumes in the wells of a 96 well plate.

Figure 17:
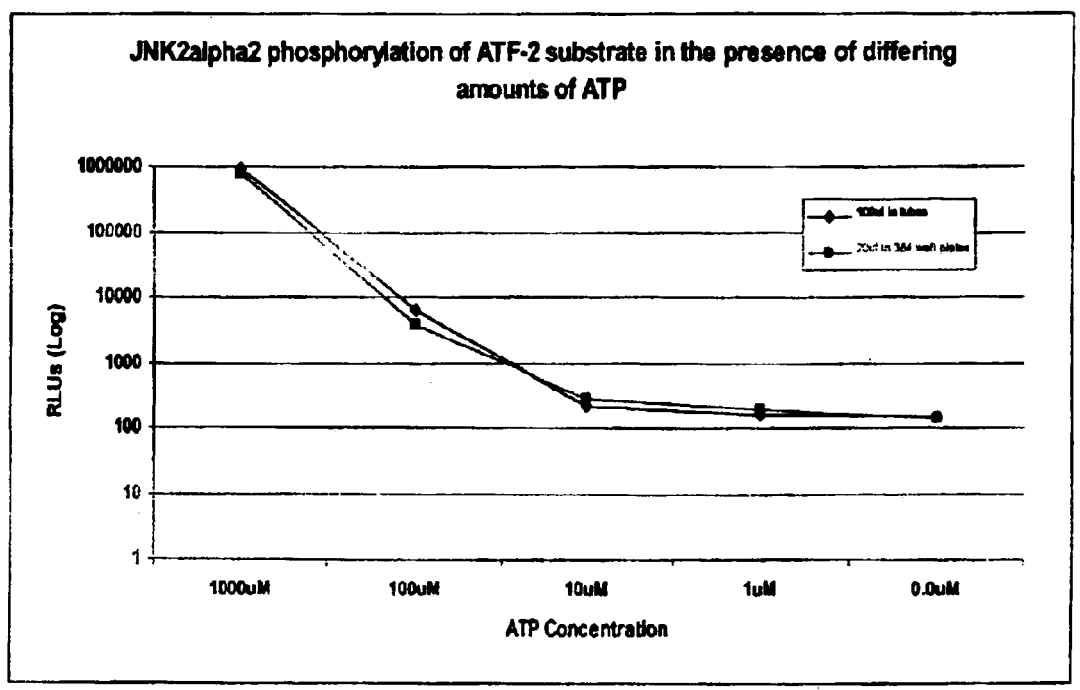
FIG. 17: Shows a comparison of performance of the kinase assay when using 20 $\mu$l from a larger reaction volume and when the assay is performed directly in the wells of a 384 well microtitre plate.

FIG. 17 shows a comparison of performance of the assay when using 20 μl from a larger reaction volume and when the assay is performed directly in the wells of a 384 well microtitre plate. In 384 wells, the kinase reaction is performed in 20 μl volumes with the addition of 20 μl of ATP detection reagent. The data show that there was no difference in the performance of the assay when carried out in tubes (100 μl) or 384 well plates (20 μl).

Example 12

Study of Kinase Cascades

The activation of kinases is most often the result of phosphorylation by other kinases upstream in the signal transduction pathways. An example of this is the activation of MAPK-2 by MEK-1, followed by MAPK-2's ability to phosphorylate MBP. We used this system to confirm that MAPK-2 had been phosphorylated and activated by MEK-1. If the protein had been activated, there would be a reduction in ATP when MAPK-2 was subsequently exposed to MBP in the presence of ATP. The assay was performed in tubes in 100 μl volumes, the initial activation of inactive MAPK2 was performed at 30° C. with 10 μM ATP. The assay buffer comprised 25 mM Tris acetate pH 7.75 with 0.1 mM EGTA and 10 mM magnesium acetate. MEK-1 was used at a final concentration of 114 nM with inactive MAPK-2 at a final concentration of 516 nm.

To determine kinase activity, 20 μl was then added to duplicate wells of a 96 well plate, and 20 μl of ATP detection reagent added and the light signal determined over a 1 second integral.

A second plate had been set up containing triplicate wells with 10 μl of MBP (Calbiochem) at 0.25 mg/ml, 10 μl of 10 μM ATP and 60 μl of assay buffer, to this 20 μl of the MEK-1/MAPK2 reaction mixture from the tubes was added, and the reaction allowed to proceed in an incubator at 30° C. for 30 minutes. After this time 20 μl of ATP detection reagent was added to the wells and the light output was determined.

Figure 18:
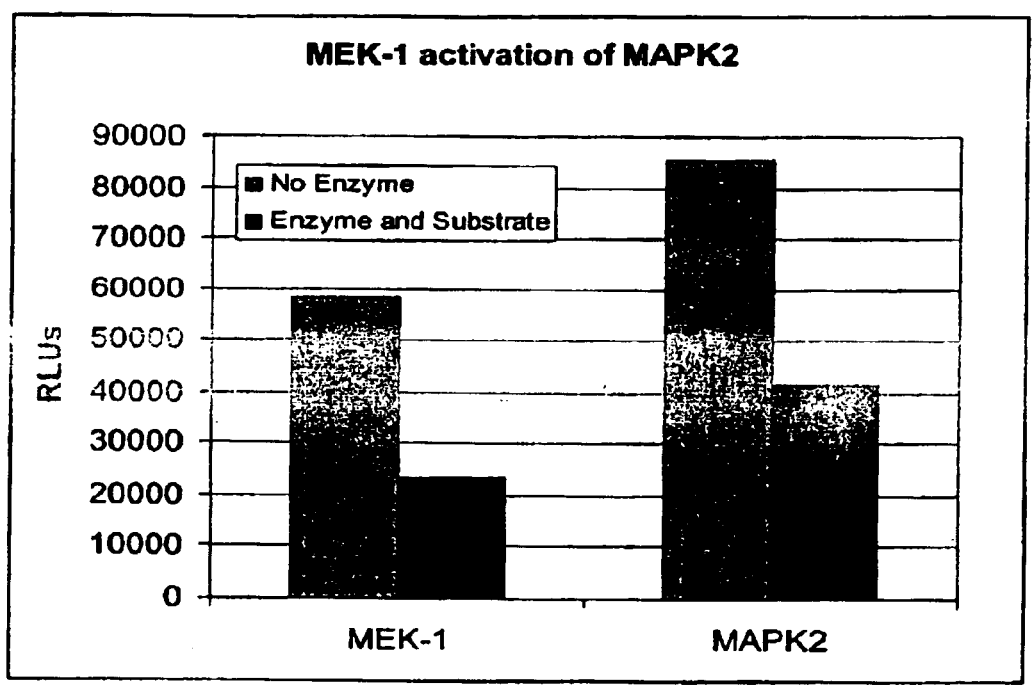
FIG. 18: Shows the activation of MAPK2 by MFK-1, followed by the phosphorylation of MBP by the previously activated MAPK-2.

The results are shown in the following FIG. 18 wherein an increase in the RLUs in the substrate only controls is observed, which relates to addition of ATP from the original MEK-1/MAPK-2 reaction mixture. The data clearly show that the MAPK-2 had been phosphorylated and was therefore able to exhibit kinase activity itself in the presence of MBP. An additional control was run with the inactive MAPK-2 and MBP which showed no drop in light signal.

Example 13

Western Blotting Studies of Substrate Phosphorylation

In addition to showing that we could induce functional activity of kinases, and detect this using the bioluminescent assay, we confirmed that the drop in light output was associated with phosphorylation of amino acids on peptide/protein substrates by Western Blotting.

Methods

Sample Preparation: After completion of the kinase reaction in 100 μl volumes, 20 μl of reaction mixture was added to 20 μl of 2× Laemmli sample buffer (Amersham, Bucks, UK) and heated at 100° C. for 4 minutes, before being placed immediately on ice until required.

A molecular weight HRP protein marker. (New England BioLabs) was prepared by adding 10 μl of marker to 10 μl of Western blotting sample buffer.

Gel Electrophoresis (SDS PAGE) and Transfer Blot: 20 μl of each of the prepared samples (equivalent to 10 μl of kinase reaction mixture) was added into the lane wells of a 12% SDS Ready Gel (BioRad, Herts, UK) and run with a standard Tris-Glycine running buffer for 45 minutes at 180 V.

The gel was equilibrated in standard Tris-Glycine-Methanol transfer buffer for 5 minutes at room temperature, before transfer to nitrocellulose membrane using the BioRad mini blot apparatus at 100 V for 60 minutes.

Membrane Probing: The membrane was blocked with Pierce Superblocke (IL, USA) blocking buffer for 1 hour at room temperature. Primary antibodies used were supplied by Promega (Wisconsin, USA) for MAPK, p38 and JNK, and by UBI for anti-phosphorylated MBP. Antibody dilutions were made in Superblock® diluted 10 fold in distilled water. The primary antibody was used at 1:10000, and where appropriate secondary antibodies at 1:20000. The HRP conjugated detection reagent was used at 1:10000 for detection of the HRP protein marker.

Chemiluminescent Detection: Probed membranes were incubated with 10 mls of SuperSignal® West Pico (Peirce, Ill. USA) for 2 minutes with slight agitation. The probed blots were then exposed to Hyperfilm (Amersham, Bucks, UK) for 20 seconds. Phosphorylated targets were compared against the molecular weight markers for identification.

Results

Figure 19:
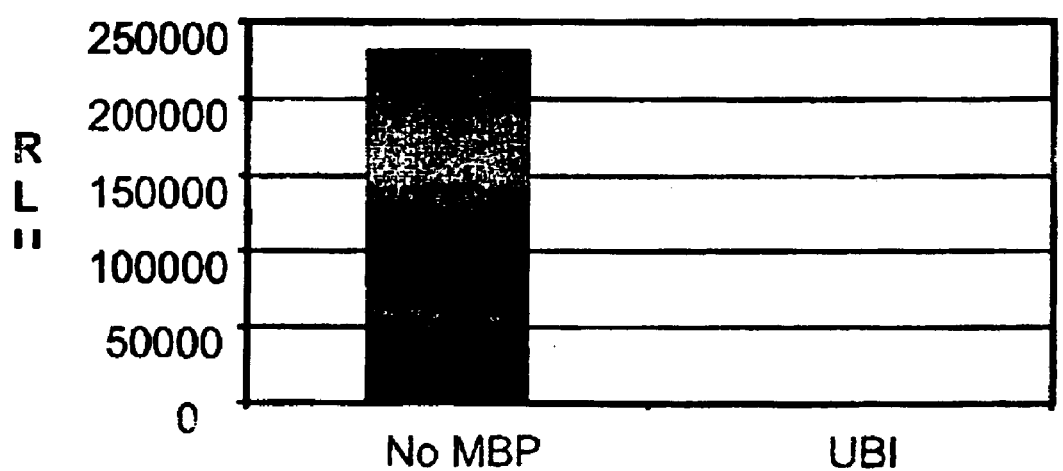
FIG. 19: Shows the correlation of a drop in light signal with the immunostaining of the phosphorylated MBP by western blotting. The left hand lane on the blot correlates with the no MBP control, and the right hand lane shows the effect of SAPK3 activity on Upstate Biotechnology (UBI) MBP.
Figure 19:
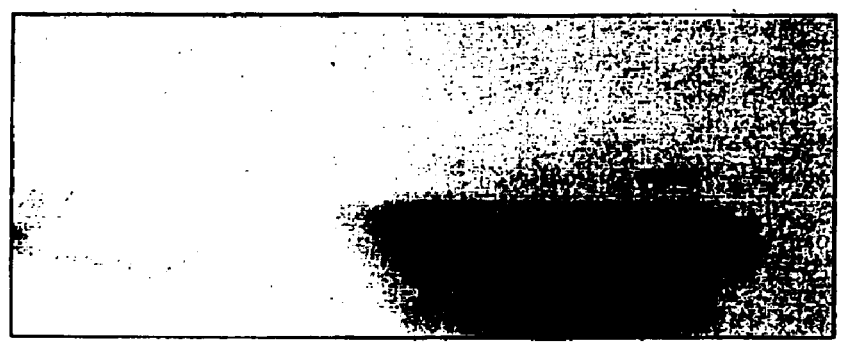

FIG. 19 shows the effect of SAPK3 activity on MBP after 30 minutes at 30° C. In this experiment, the assays were run in tubes as described previously. For determination of ATP levels, a 20 μl aliquot of sample was removed into duplicate wells of a 96 well luminescent compatible plate, and the remainder used for Western blotting analysis. The blot was probed using an antibody to phosphorylated MBP (Upstate Biotechnology).

Figure 20:
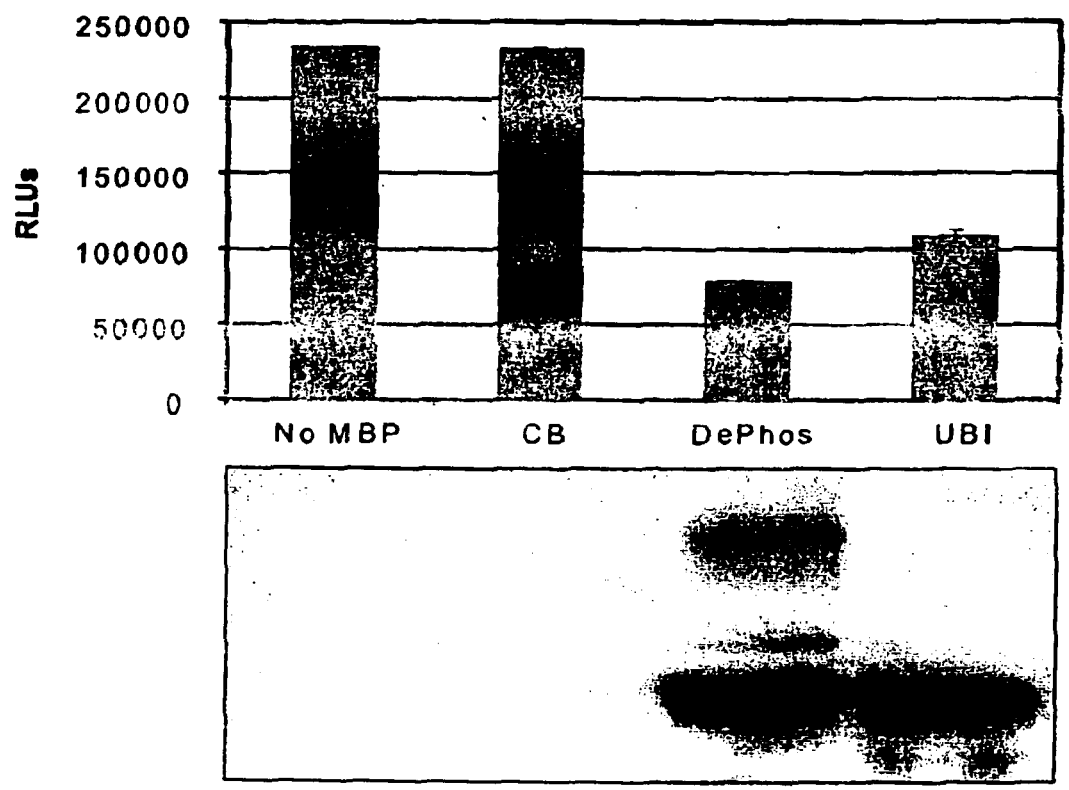
FIG. 20: Shows a comparison between the bioluminescent assay of kinase activity and the results of the Western blotting.

The above experiment was repeated using SAPK4 and a number of different supplies of MBP. The results are shown in FIG. 20, and highlight that some proteins, even when used at the same concentrations gave different results with both the bioluminescent assay and Western blotting. The blots were again probed with the same anti-phosphorylated MBP. As the results show, one of the batches of MBP used (CB) had no effect in either detection assay. Two different samples of MBP were used from Upstate Biotechnology, one was the dephosphorylated form (DePhos) and the other standard MBP (UBI). The bioluminescent data suggested that for the same amount of protein used (2.72 $\mu$M), the dephosphorylated form was more efficient in the SAPK4 assay. This could not be determined from the inmunoblotting, confirming that bioluminescence is a more sensitive and quantitative assay for kinase activity.

Summary

The studies described in Examples 1 to 13 above demonstrate the versatility of the methods and kits of the present invention.

In particular, the methods of the invention may be used to study a number of different protein kinase/substrate combinations. The protein kinase enzymes used in the above examples included:
- (i) JNK-1 and JNK-2 in the presence of c-jun peptide as substrate;
- (ii) MAPK-1/ERK-1 and MAPK-2/ERK-2 with myelin basic protein as substrate;
- (iii) MEK-1 with inactive MAPK-2 as substrate;
- (iv) JNK2α2 with ATF-2 and c-jun as substrates;
- (v) SAPK-3 with myelin basic protein as substrate; and
- (vi) SAPK-4 with myelin basic protein as substrate;

In addition, comparisons were made between the activated and inactive forms of both MAPK-1/ERK-1 and MAPK-2/ERK-2 in the presence of myelin basic protein.

The results from these experiments show that it was possible to detect kinase activity in the presence of ATP and the appropriate enzyme substrate, through a decrease in detectable ATP, an increase in measured ADP, and also accelerated signal decay in the presence of luciferase.

Several advantages of the assays of the invention are summarised in the following points.

- The assay can be applied to any protein kinase that cleaves a phosphate from ATP.
- The protein kinase activity could be allowed to go to completion, prior to detection of ATP and/or ADP.
- The assay could be performed in the presence of the ATP monitoring reagent, with protein kinase activity being determined as a drop in light output, together with an increase in signal decay.
- Changes in adenylate nucleotides showed a concentration dependent effect with variations in enzyme, substrate and ATP concentrations.
- The drop in light signal correlates with protein phosphorylation.
- The methods can be used to detect and study protein kinase inhibitors.
- The methods can be used to study protein kinase cascade systems.
- The assays could be performed at room temperature or 30° C.
- Changes in adenylate nucleotides could be detected in the presence or absence of a stop solution, permitting mass screening of samples. By using an appropriate buffer (e.g. Hepes), it was also possible to stop the protein kinase reaction with 2% phosphoric acid and detect the reduced amount of ATP as a result of protein kinase activity.
- The methods can be used with a number of different protein kinase buffers
- The ATP detection reagent can be used in either Tris acetate or Hepes buffers.
- The assay can be supplied as a kit. Different kits could be supplied for measurement of drop in ATP, with or without the use of a stop reagent. The kits could also contain the ADP converting reagent (as outlined in appendix 1), for detecting an increase in ADP as a result of protein kinase activity.

Applications of the Methods of the Invention

The methods and assays of the present invention, as described in the above examples can be used as a measure of kinase activity in cell free systems. This is of particular importance in the pharmaceutical industry since it enables the methods and assays to be used in high throughput screening laboratories, e.g. for identification of drugs that can act as kinase modulators, especially inhibitors. For this application, the assays can be carried out exactly as described in the above examples.

The methods and assays of the invention may also be used to determine kinase activity in cellular extracts, and to determine the effect of modulators of cellular kinase activity. To perform these experiments, it is possible to substitute the known kinase in the above examples for the cell extract/supernatant. The substrate is added as described, and any changes in kinase activity in cells treated with inhibitors/activators can be detected.

There is an increasing number of protein kinases that are being targeted for the development of new tumour therapeutics. As this list increases it will become impractical and extremely expensive to use specific tests for each kinase. The assays and kits of the present invention allow for the detection of a wide spectrum of kinases and provide a common end point detection system for all kinases. This allows for greater ease of use, particularly in high throughput screening laboratories, where robots can be set up with all the detection reagents and the various kinases and inhibitors, of interest, and with opaque white (or black) luminometer microtitre plates.

Moreover, the use of a stop solution allows for a large number of plates to be batched up (i.e. stored) prior to analysis of ATP and/or ADP levels.

Example 14

Study of Kinase Inhibitors

Staurosporine

We initially chose to look at a broad spectrum kinase inhibitor staurosporine (Calbiochem). Firstly, we tested the inhibitor (in DMSO) on the ATP detection reagent to ensure that the inhibitor would not affect the luciferase-luciferin reaction.

Figure 21:
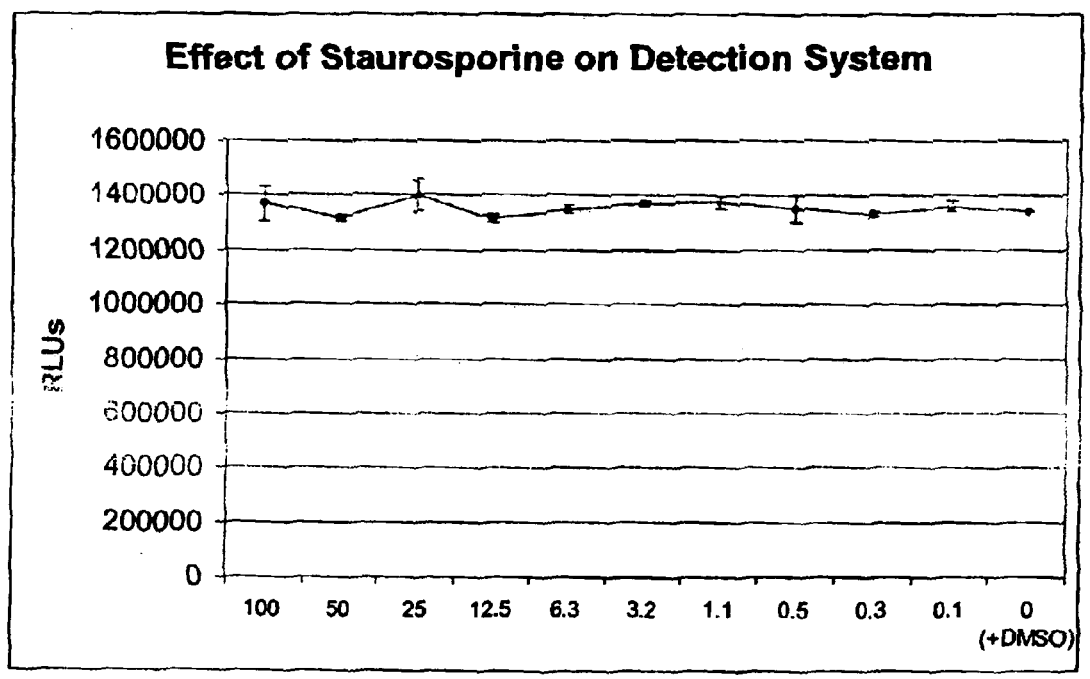
FIG. 21: Shows the effect of staurosporine on the bioluminescent detection system. The results are presented as the means of triplicate wells ±SD.

FIG. 21 shows the effect of staurosporine on the bioluminescent detection system. The results are presented as the means of triplicate wells±SD.

Data show that, even at the highest concentration of the inhibitor, there was no significant effect upon light output. The experiment was performed using 10 $\mu$M ATP in 100 $\mu$l volumes in a 96 well plate with the addition of 20 $\mu$l of ATP detection reagent.

The effect of staurosporine was tested on the JNK2α2 enzyme with ATF-2 as substrate, and as the following figure shows the expected inhibitory activity could be detected using the bioluminescent protein kinase assay system.

Figure 22:
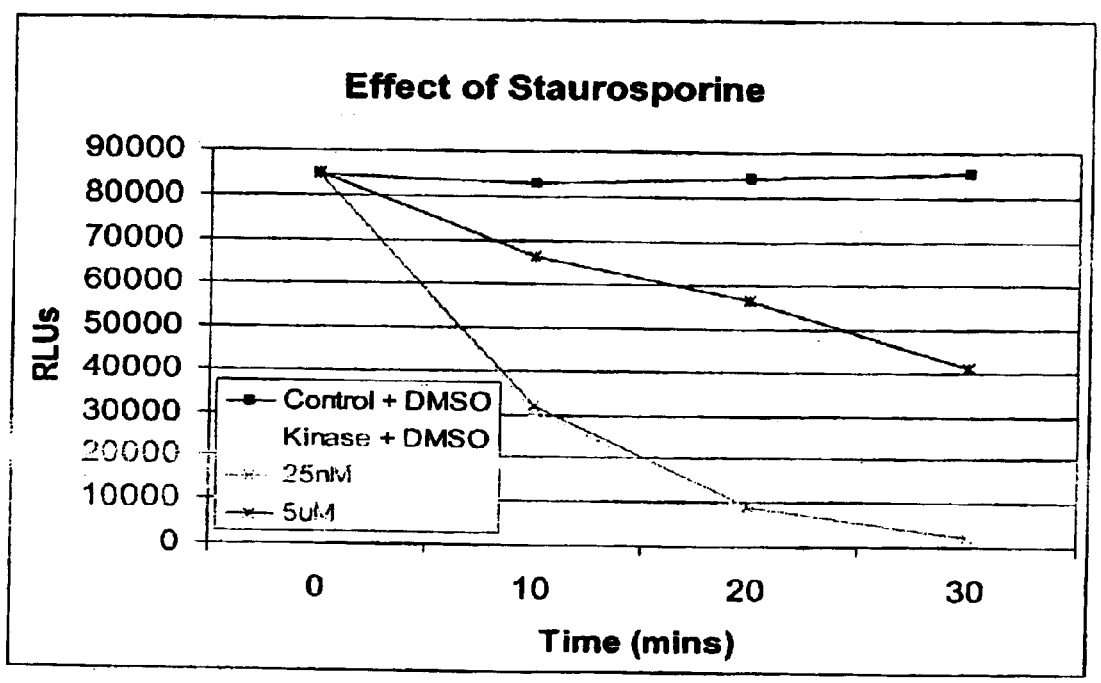
FIG. 22: Shows the effect of two different staurosporine concentrations on JNK2$\alpha$2 activity (with ATF-2 as substrate).

FIG. 22 shows the effect of two different staurosporine concentrations on JNK2α2 activity. The lower concentration had little effect, however 5 μM caused approximately 50% inhibition after 30 minutes at 30° C.

The above assay was performed in 200 μl volumes in plastic tubes in, a 30° C. waterbath. At each time point 20 μl samples were removed from the tubes and added to wells of a 96 well plate, followed by the addition of 20 μl of ATP detection reagent. The final concentration of ATP used was 12.5 μM, with JNK2α2 at 1.25 μM and ATF-2 at 2.55 μM.
Genistein We also investigated the effect of genistein (Calbiochem) on MAPK-1 activity with MBP as substrate.

The assay buffer used was the same as for the SAP kinases (see above). The assay was performed in 100 μl volumes in a 96 well microtitre plate at 30° C. for 30 minutes. MBP (Calbiochem) was used at the same concentration as previously described (2.72 μM), with the activated MAPK1/ERK1 (UBI) used at a final concentration of 2.5U per100 μl reaction volume. The inhibitor was added at concentrations of 0, 0.1, 0.25, 0.5 and 1.0 μM, with 10 μl being added per well in 0.1% (v/v) DMSO.

For completeness, control samples with and without DMSO (0+DMSO and 0−DMSO, respectively) were also analysed to confirm that there was no effect of DMSO on the performance of the assay.

Figure 23:
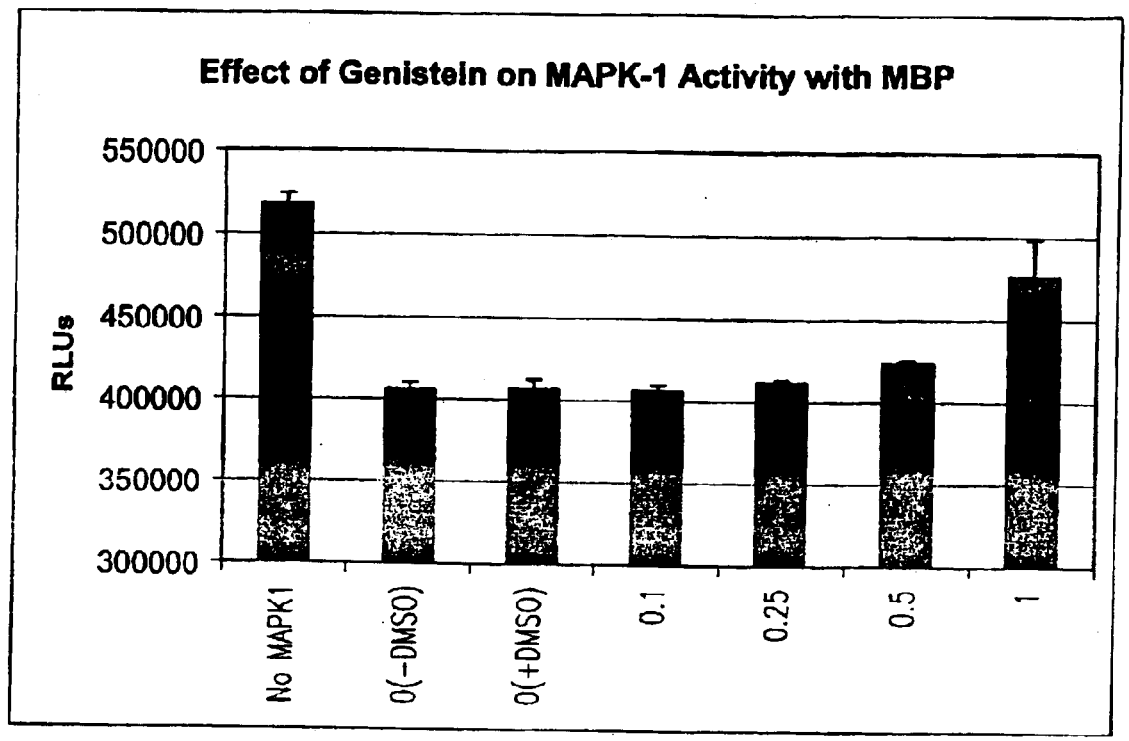
FIG. 23: Shows the effect of increasing concentrations of genistein on MAPK-1 activity (with MBP as substrate).

FIG. 23 shows the effect of increasing concentrations of Genistein (in μM) on MAPK-1 activity with MBP as substrate (results are presented as the means of duplicate wells±SD). Specifically, the data showed an effect of genistein at 500 nM, with increased inhibitory activity at 1 μM.
PD098059

We also investigated the effect of the selective inhibitor PD098059 on the raf-1 activation of inactive MEK-1.

With PD098059, there was a concentration dependent increase in the light output in the presence of the inhibitor indicating reduced kinase activity.

Figure 24:
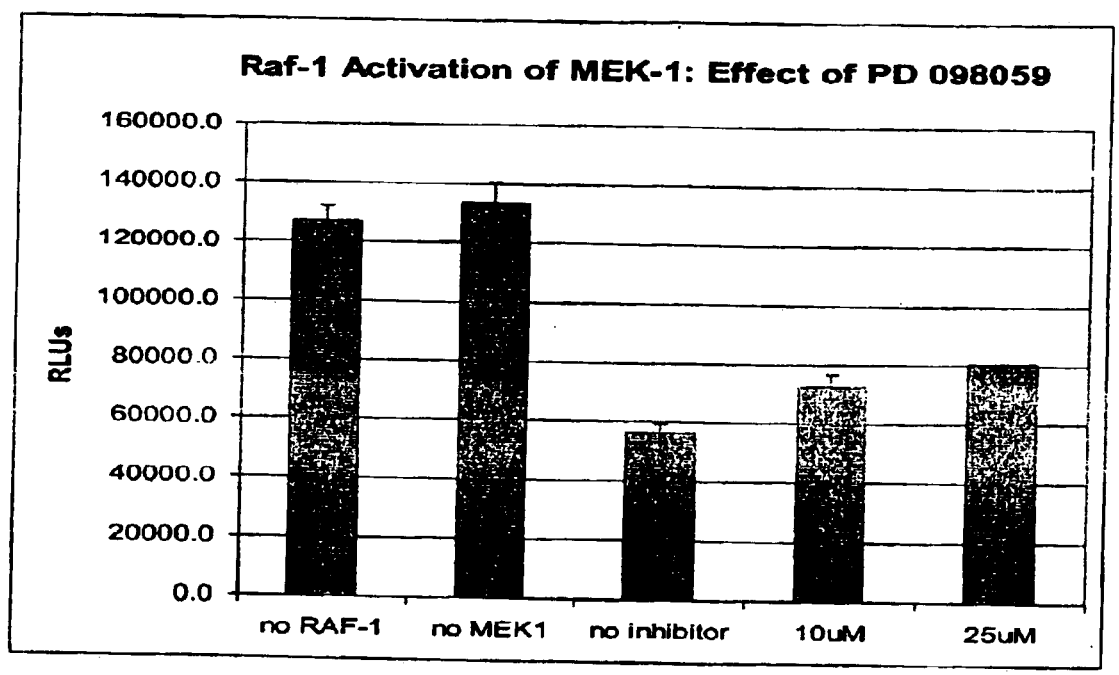
FIG. 24: Shows the effect of two different concentrations of PD098059 on raf-1 activity (with inactive MEK-1 as substrate). The results are the means of triplicate wells±SD.

FIG. 24 shows the effect of two different concentrations of PD098059 on raf-1 activity (results are the means of triplicate wells±SD). These data confirmed the suitability of the assay for determination of kinase inhibitory activity.

This experiment also provides evidence of the versatility of methods and assays of the present methods since it was possible to detect activity of another kinase/substrate system, namely raf-1/inactive MEK-1.

Appendix 1
ATP Detection Reagent (ADR) Formulation

| Reconstituted ADR | | |
|---|---|---|
| Magnesium acetate | 20 mM | Sigma |
| Tetrasodium pyrophosphate | 8 μM | Sigma |
| Bovine Serum Albumin | 0.32% w/v | Sigma |
| D-Luciferin | 712 μM | ConCell |
| L-Luciferin | 17.8 μM | ConCell |
| Luciferase | 17 nM | Europa Bioproducts |
| Dextran | 3 mg ml$^{-1}$ | Sigma |
| Tris | 40 mM | Sigma |
| EDTA | 800 μM | Sigma |

| Final Reaction Concentrations | |
|---|---|
| Magnesium acetate | 2.36 mM |
| Tetrasodium pyrophosphate | 236 nM |
| Bovine Serum Albumin | 0.009% w/v |
| D-Luciferin | 21 μM |
| L-Luciferin | 525 nM |
| Luciferase | 500 pM |
| Dextran | 88.5 g ml$^{-1}$ |
| Tris | 1.18 mM |
| EDTA | 23.6 μM |

Tris Acetate (TA) Buffer (Sufficient for 1 Litre)

| Tris | 12.1 g | Sigma |
|---|---|---|
| EDTA | 0.744 g | Sigma |

0.1M Tris, 2 mM EDTA adjust to pH 7.75 with glacial acetic acid.
Hepes Buffer 200 mM (Sufficient for 1 Litre)

| EDTA | 0.744 g | Sigma |
|---|---|---|
| Hepes | 47.6 g | Sigma |

Adjust to pH 7.75 with glacial acetic acid
UBI Buffer (as Per UBI Data Sheet)
20 mM MOPS pH7.2
25 mM β-glycerol phosphate
5 mM EGTA
1 mM sodium orthovanadate
1 mM dithiothreitol
JNK Assay Buffer (Formulation for ×10 concentrate)

| 250 mM Hepes, pH 7.5 | Sigma |
|---|---|
| 1.5M Sodium Chloride | Sigma |
| 200 mM Magnesium Chloride | Sigma |
| 0.01% Tween 20 | Sigma |

At time of use there is the addition of 20 mM dithiothreitol (Sigma) and 150 μM ATP (Sigma).
ADP Converting Reagent (Sufficient for 600 mls)

| Pyruvate kinase (50 000 Units) | 20 ml | Calbiochem |
|---|---|---|
| 1M Phosphoenol pyruvate (monosodium salt) | 10 ml | Sigma |
| 2M Potassium Acetate | 100 m | Sigma |
| Tris acetate buffer pH 7.75 | 470 ml | |

Final Concentrations:

| | Stock | Reaction Mixture |
|---|---|---|
| PK | 7.6 U/ml | 0.8 U/ml |
| PEP | 1.67 mM | 175 nM |
| Potassium acetate | 33 mM | 3.5 mM |

Appendix 2: Suppliers

APPENDIX 2

| Suppliers |
|---|
| Berthold Detection Systems GmbH |
| Bleichstrasse 56–58 |
| D-75173 Pforzheim |

APPENDIX 2-continued

Suppliers

Germany
Biotrace Ltd
The Science Park
Bridgend
CF31 3NA
Calbiochem-Novabiochem (UK) Ltd
Boulevard Industrial Park
Padge Road
Beeston
Nottingham NG9 2JR
ConCell BV
Wevelinghoven 26
Nettetal
D-41334
Germany
Europa Bioproducts Ltd
Europa House
15–17 North Street, Wicken
Ely, Cambridge
CB7 5XW
Fahrenheit Lab Supplies
Northfield Road
Rotherham
Dynex Labsystems
Action Court
Ashford Road
Ashford
Middlesex TW15 1XB
Labsystems Oy
Sorvaajankatu 15
Helsinki
Finland
00810
Perkin Elmer Life Sciences
Perkin Elmer House
204 Cambridge Science Park
Cambridge CB4 0GZ
Sarstedt
68 Boston Road
Beaumont Leys
Leicester LE4 1AW
Sigma-Aldrich Co Ltd
Fancy Road
Poole
Dorset BH12 4QH
Upstate Biotechnology Inc. (UBI)
199 Saranac Avenue
Lake Placid
NY 12946

What is claimed is:

1. A method for measuring protein kinase activity comprising:
   (1) establishing a first solution comprising ATP, a protein kinase to be tested and a substrate capable of being phosphorylated by the protein kinase to be tested;
   (2) establishing a second solution comprising ATP and said substrate;
   (3) adding a bioluminescent reagent to said first and second solutions and
   (4) measuring the intensity of light emitted or a change in light intensity with respect to time in said first and second solutions, as a measure of ATP concentration, whereby the measure of ATP concentration is related to said protein kinase activity.

2. A method for identifying a compound which modulates the activity of a protein kinase, said method comprising:
   (1) establishing a first solution comprising ATP, a protein kinase to be tested, a substrate capable of being phosphorylated by the protein kinase to be tested and a compound to be tested;
   (2) establishing a second solution comprising ATP, said protein kinase and said substrate;
   (3) adding a bioluminescent reagent to said first and second solutions and
   (4) measuring the intensity of light emitted or a change in light intensity with respect to time in said first and second solutions, as a measure of ATP concentration, whereby the measure of ATP concentration is related to said protein kinase activity and any effect of said compound on said protein kinase activity.

3. The method of claim 1 wherein the first and second solutions are substantially cell-free.

4. The method of claim 2 wherein the first and second solutions are substantially cell-free.

5. The method of claim 2 or 4 wherein the compound to be tested is identified as a protein kinase inhibitor if the activity of the kinase in the first solution is lower than the activity of the kinase in the second solution.

6. The method of claim 5 wherein the compound to be tested is identified as a protein kinase inhibitor if the activity of the kinase in the first solution is less than 50% of the activity of the kinase in the second solution.

7. The method of claim 2 or 4 wherein the compound to be tested is identified as a protein kinase activator if the activity of the kinase in the first solution is higher than the activity of the kinase in the second solution.

8. The method of claim 7 wherein the compound to be tested is identified as a protein kinase activator if the activity of the kinase in the first solution is at least 50% greater than the activity of the kinase in the second solution.

9. The method of claim 2 further comprising repeating steps (1) to (4) one or more times using a different kinase and corresponding substrate each time.

10. The method of claim 2 wherein the kinase is activated prior to steps (1) and (2).

11. The method of claim 1 or 2 wherein the first or second solutions comprise Hepes buffer.

12. The method of claim 2 comprising a further step (2'), carried out after steps (1) and (2) and before step (3), of adding a stopping reagent to the solutions established in steps (1) and (2) which stops reaction of the kinase with the substrate.

13. The method of claim 12 wherein the stopping reagent is selected from the group consisting of phosphoric acid, EGTA and EDTA.

14. The method of claim 12 comprising a further step (2"), carried out after step (2') and before step (3), of adjusting the pH of the mixtures formed in step (2') to pH 7.0.

15. The method of claim 14 wherein step (2") comprises adding Hepes buffer.

16. The method of claim 1 or 2 wherein step (3) comprises:
   (i) adding luciferin or a derivative thereof and a luciferase to said solutions, said luciferin or a derivative thereof emitting light in a bioluminescent reaction with the luciferase in the presence of ATP.

17. The method of claim 16 wherein step (3) further comprises the following steps carried out after the light intensity measured in step (4) has reached a substantially constant level:
   (5) adding a reagent that converts ADP to ATP;
   (6) adding a bioluminescent reagent comprising luciferin or a derivative thereof and luciferase to said reaction mixture of step (5); and
   (7) measuring the intensity of light emitted by the resultant bioluminescent reaction wherein the difference in the intensity of light in step (7) and the steady state intensity of light in step (4) is a measure of ADP concentration.

18. The method of claim 2 wherein the kinase is JNK-1 and the substrate is GST-c-jun.

19. The method of claim 2 wherein the kinase is MAP Kinase-1 (ERK-1) and the substrate is myelin basic protein.

20. The method of claim 2 wherein the kinase is MAP Kinase-2 (ERK-2) and the substrate is myelin basic protein.

21. The method of claim 2 wherein the kinase is PKA and the substrate is Kemptide.

22. The method of claim 2 wherein the kinase is JNK-2 and the substrate is GST-c-jun.

23. The method of claim 2 wherein the kinase is MEK-1 and the substrate is inactive MAP Kinase-2 (ERK-2).

24. The method of claim 2 wherein the kinase is JNK2α2 and the substrate is ATF-2.

25. The method of claim 2 wherein the kinase is JNK2α2 and the substrate is c-jun.

26. The method of claim 2 wherein the kinase is SAPK-3 and the substrate is myelin basic protein.

27. The method of claim 2 wherein the kinase is SAPK-4 and the substrate is myelin basic protein.

28. The method of claim 2 wherein the kinase is raf-1 and the substrate is inactive MEK-1.

29. A compound identified using a method according to claim 2.

* * * * *